(12) United States Patent
Zhang et al.

(10) Patent No.: US 12,740,716 B1

(45) Date of Patent: Sep. 22, 2026

(54) SYSTEM AND METHOD FOR CAPTURING AND TRANSMITTING BIOMETRIC DATA

(71) Applicant: Nexa Labs Inc., Great Falls, VA (US)

(72) Inventors: Alvin Zhang, San Francisco, CA (US); Zarif Azher, San Francisco, CA (US); Kenneth Chan, San Francisco, CA (US); Kyle Berkson, San Francisco, CA (US)

(73) Assignee: Nexa Labs Inc., Great Falls, VA (US)

( * ) Notice: Subject to any disclaimer, the term of this patent is extended or adjusted under 35 U.S.C. 154(b) by 0 days.

(21) Appl. No.: 19/331,418

(22) Filed: Sep. 17, 2025

Related U.S. Application Data

(60) Provisional application No. 63/860,299, filed on Aug. 8, 2025, provisional application No. 63/860,264, filed (Continued)

(51) Int. Cl.

| | |
|---|---|
| ***A61B 5/0205*** | (2006.01) |
| ***A01K 11/00*** | (2006.01) |
| ***A61B 5/00*** | (2006.01) |
| ***A61B 5/07*** | (2006.01) |
| ***A61B 5/1455*** | (2006.01) |
| *A61B 5/024* | (2006.01) |
| *A61B 5/08* | (2006.01) |
| *H02J 50/10* | (2016.01) |

(52) U.S. Cl.

CPC ........ *A61B 5/02055* (2013.01); *A01K 11/004* (2013.01); *A61B 5/076* (2013.01); *A61B 5/14552* (2013.01); *A61B 5/6861* (2013.01); *A61B 5/02405* (2013.01); *A61B 5/0816* (2013.01); *A61B 2503/40* (2013.01); *A61B 2560/0209* (2013.01); *A61B 2560/0219* (2013.01); *A61B 2562/0271* (2013.01); *A61B 2562/162* (2013.01); *A61B 2562/166* (2013.01); *H02J 50/10* (2016.02)

(58) Field of Classification Search

CPC .......................... A01K 11/006; A61B 5/02055

See application file for complete search history.

(56) References Cited

U.S. PATENT DOCUMENTS

| | | | | |
|---|---|---|---|---|
| 5,461,806 A * | 10/1995 | Bristow, Jr. .......... | A01K 11/001 40/302 |
| 2008/0276879 A1 * | 11/2008 | Marsh ................. | A01K 11/008 119/719 |

(Continued)

*Primary Examiner* — William J Levicky

(74) *Attorney, Agent, or Firm* — Run 8 Patent Group, LLC; Peter Miller; Madison Tyrcha

(57) ABSTRACT

A system includes a subdermal sensor unit and a superficial tag. The subdermal sensor unit is injectable under skin of an ear of an animal and includes: a subdermal housing; a biometric sensor sealed in subdermal housing; and a subdermal short-range wireless transmitter configured to broadcast a set of biometric data captured by the biometric sensor at a first power level via a short-range wireless communication protocol. The superficial tag includes: a tag housing; a wireless communication module configured to receive the set of biometric data broadcast by the subdermal short-range wireless transmitter in the subdermal sensor unit and transmit the set of biometric data to an access point at a second power level, greater than the first power level, via a longer-range wireless communication protocol.

18 Claims, 9 Drawing Sheets

Related U.S. Application Data on Aug. 8, 2025, provisional application No. 63/783,647, filed on Apr. 4, 2025.

(56) References Cited

U.S. PATENT DOCUMENTS

2010/0312310 A1* 12/2010 Meskens .............. A61N 1/3787
607/61
2014/0333439 A1* 11/2014 Downing ............. A01K 11/006
374/186
2017/0127975 A1* 5/2017 Bozkurt ............... A01K 11/006
2017/0132438 A1* 5/2017 Cletheroe .......... G06K 7/10356

* cited by examiner

SYSTEM AND METHOD FOR CAPTURING AND TRANSMITTING BIOMETRIC DATA

CROSS-REFERENCE TO RELATED APPLICATIONS

This application claims the benefit of U.S. Provisional Application Nos. 63/860,264 filed on 8 Aug. 2025, 63/860,299 filed on 8 Aug. 2025, and 63/783,647 filed on 4 Apr. 2025, each of which is incorporated in its entirety by this reference.

TECHNICAL FIELD

This invention relates generally to the field of animal health management and, more specifically, to a new and useful system and method for capturing and transmitting biometric data in the field of animal health management.

DESCRIPTION OF THE EMBODIMENTS

Figure 1A:
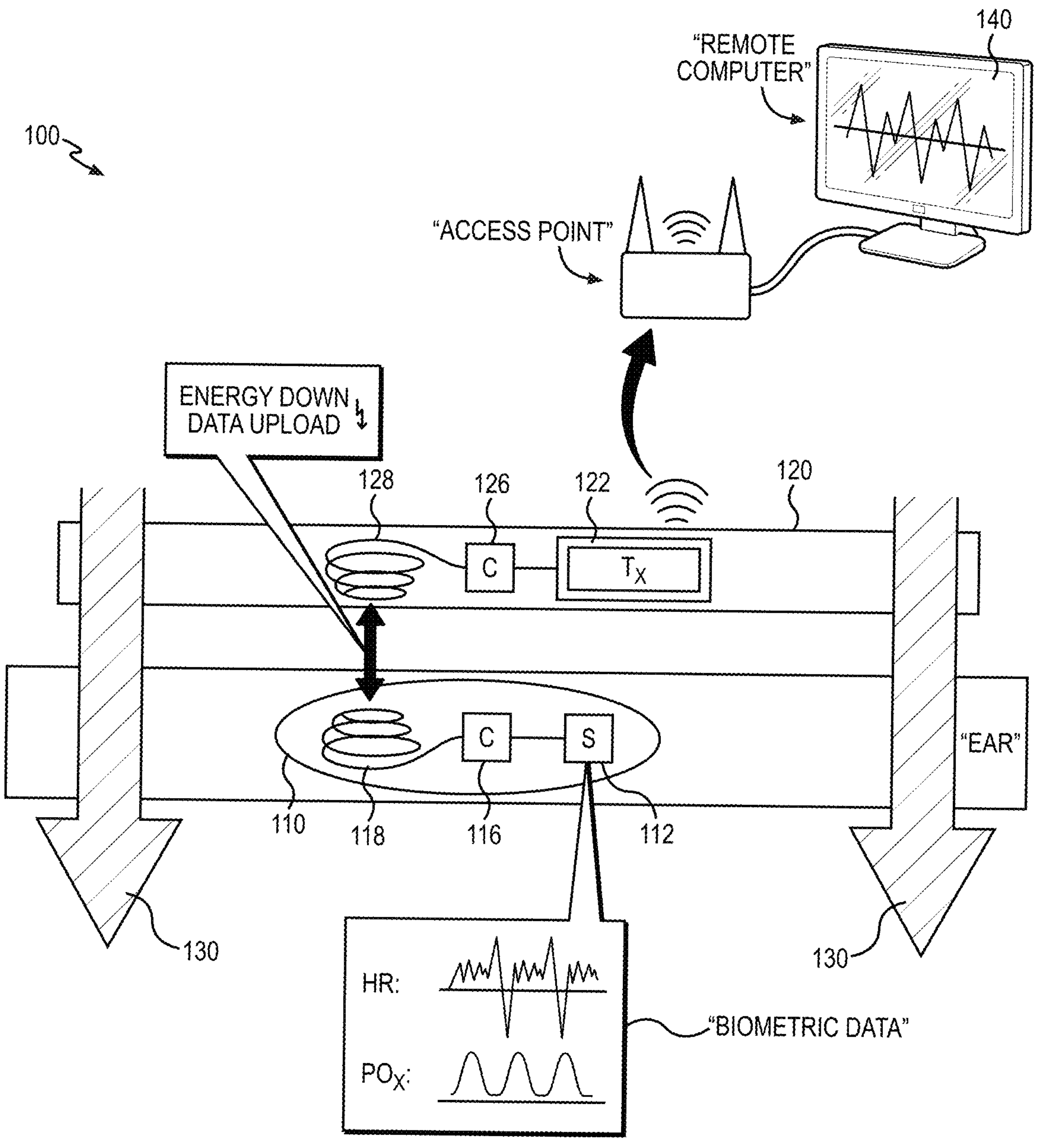
FIGS. 1A and 1B are schematic representations of a system.
Figure 1B:
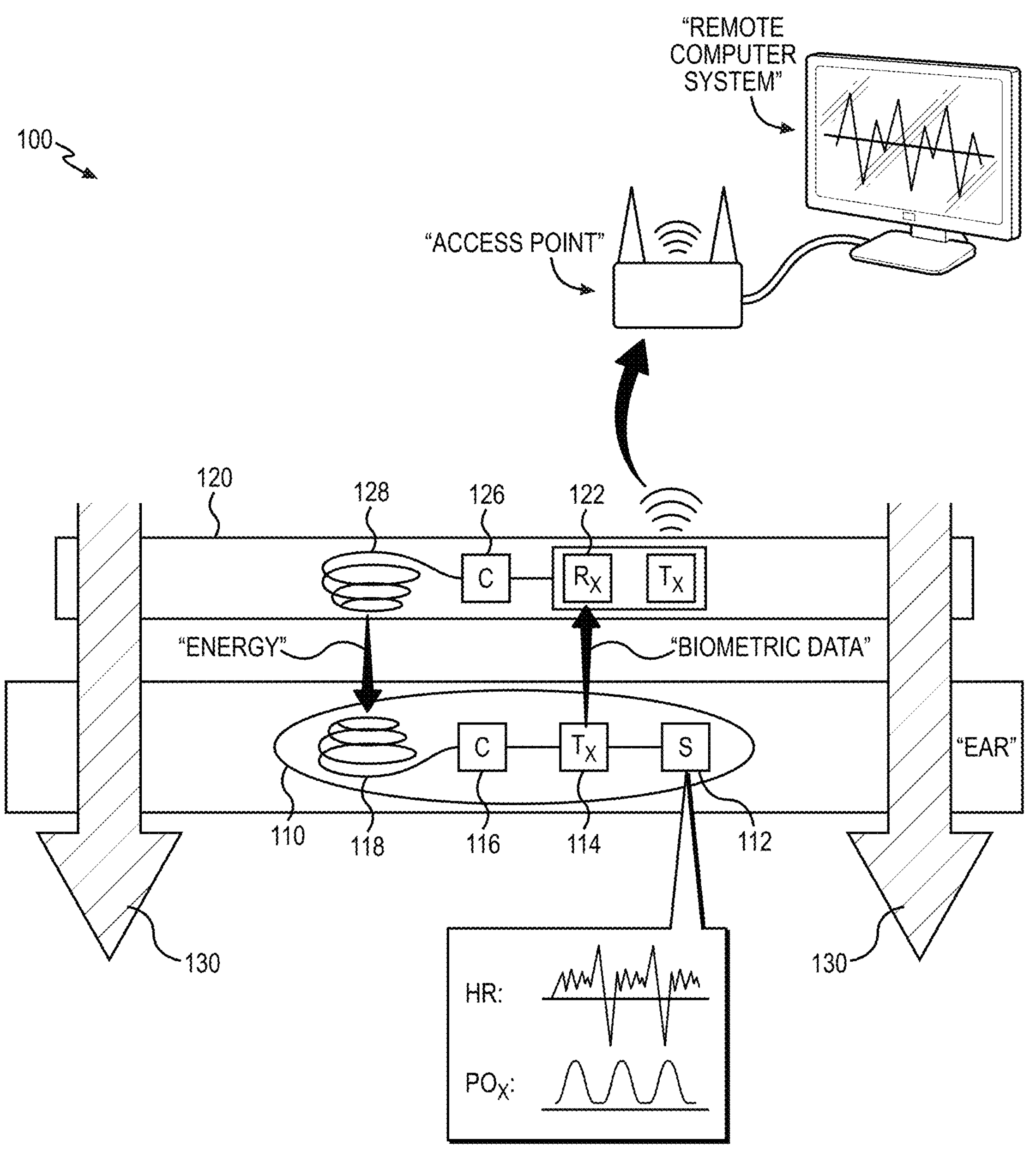
Figures 2A, 2B:
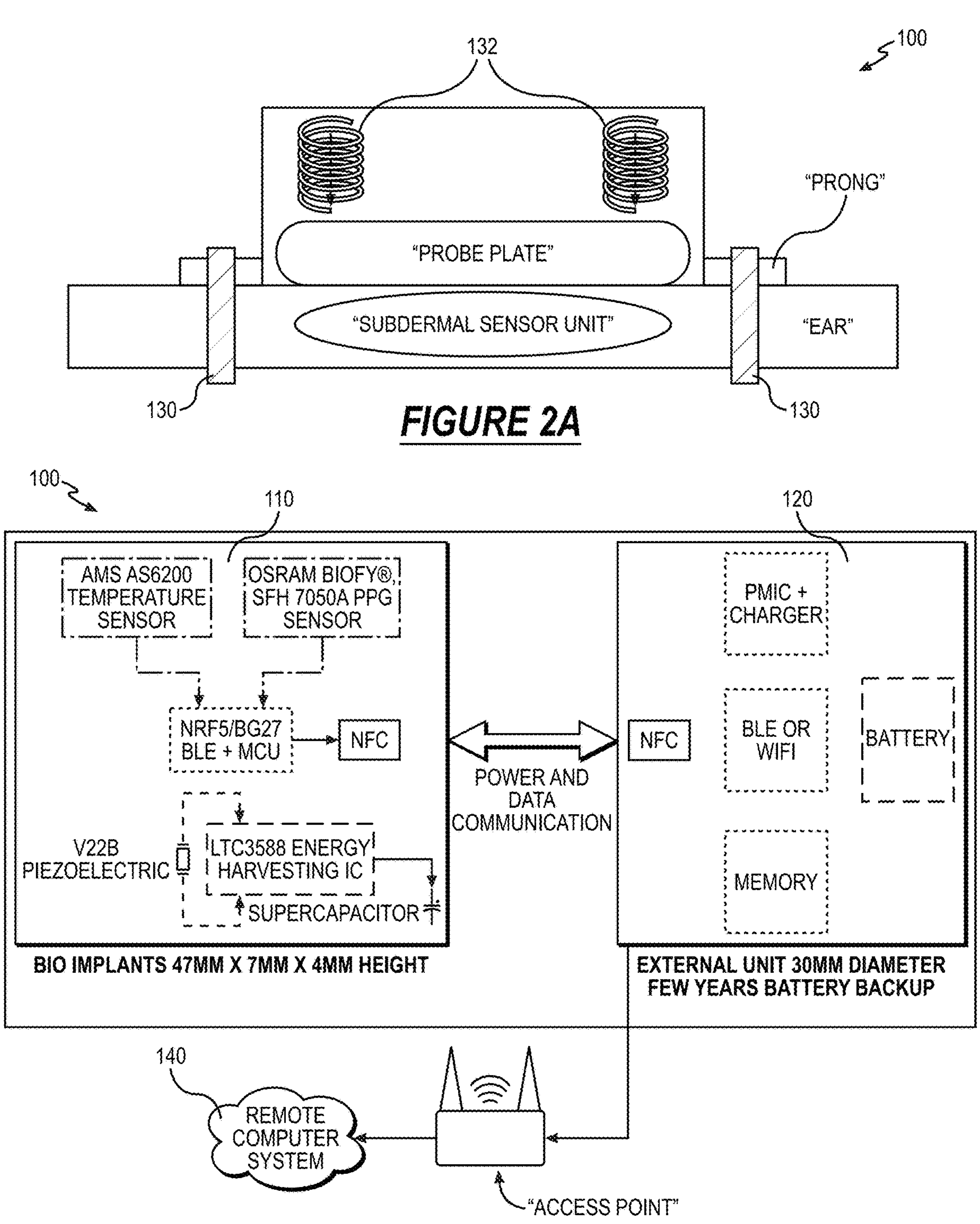
FIGS. 2A and 2B are schematic representations of one variation of the system.

The following description of embodiments of the invention is not intended to limit the invention to these embodiments but rather to enable a person skilled in the art to make and use this invention. Variations, configurations, implementations, example implementations, and examples described herein are optional and are not exclusive to the variations, configurations, implementations, example implementations, and examples they describe. The invention described herein can include any and all permutations of these variations, configurations, implementations, example implementations, and examples.

1. System

As shown in FIGS. 1A, 1B, 2A, and 2B, a system 100 includes: a subdermal sensor unit 110; and a superficial tag 120.

The subdermal sensor unit 110 is injectable under skin of an ear of an animal and includes: a subdermal housing 111; a biometric sensor 112 sealed in the subdermal housing 111; and a subdermal short-range wireless transmitter 114. The subdermal short-range wireless transmitter 114: is sealed in the subdermal housing 111; and is configured to broadcast a set of biometric data captured by the biometric sensor 112 at a first power level via a short-range wireless communication protocol.

The superficial tag 120 includes: a tag housing 121; a tag wireless communication module 122; and a set of barbs 130. The superficial wireless communication module 122: is located within the tag housing 121; includes a short-range wireless receiver configured to receive the set of biometric data broadcast by the subdermal short-range wireless transmitter 114 in the subdermal sensor unit 110; and a long-range wireless transmitter configured to transmit the set of biometric data to an access point at a second power level, greater than the first power level, via a longer-range wireless communication protocol. The set of barbs 130 is configured to pass through the ear of the animal: to retain the tag housing 121 on the ear of the animal with the short-range wireless receiver located over the subdermal short-range wireless transmitter 114; and to maintain wireless connectivity between the subdermal short-range wireless transmitter 114 and the short-range wireless receiver.

1.1 Coupled Wireless Charging and Data Transmission

As shown in FIG. 2, in one variation of the system 100: the superficial wireless communication module further includes an inductive charging cell configured to: transmit power to the subdermal sensor unit (e.g., via inductive or resonant coupling); and receive biometric data from the subdermal short-range wireless transmitter (e.g., via load modulation).

In this variation, the subdermal sensor unit further includes a subdermal communication module: housed within the subdermal sensor unit; including the subdermal short-range wireless transmitter and an inductive charging coil; and configured to transmit biometric data to the tag wireless communication module (e.g., via load modulation) and receive power from the inductive charging cell in the superficial tag (e.g., via inductive or resonant coupling).

1.2 Decoupled Wireless Charging and Data Transmission

In another variation of the system 100, the superficial tag includes an inductive charging coil distinct from the short-range wireless receiver. In this variation, the subdermal sensor unit includes: a local energy store (e.g., a battery, a capacitor); an inductive charging coil distinct from the subdermal short-range wireless transmitter and configured to power (or charge) the local energy store; and the subdermal short-range wireless transmitter configured to broadcast a set of biometric data to the short-range wireless receiver over a sampling interval responsive to receiving power from the local energy store.

1.3 Variation: Controls+Method

Figure 3:
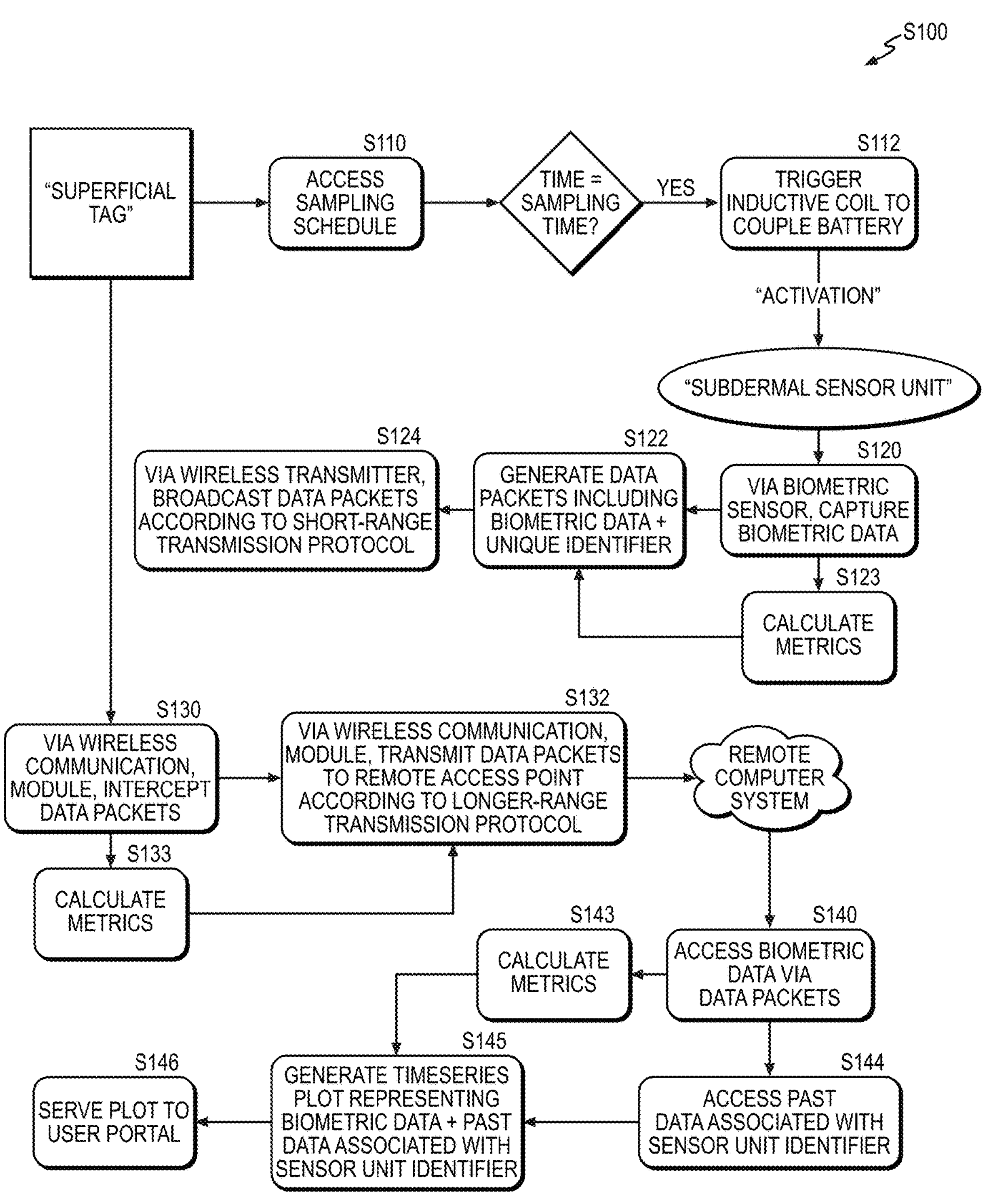
FIG. 3 is a flowchart representation of a method.
Figure 4:
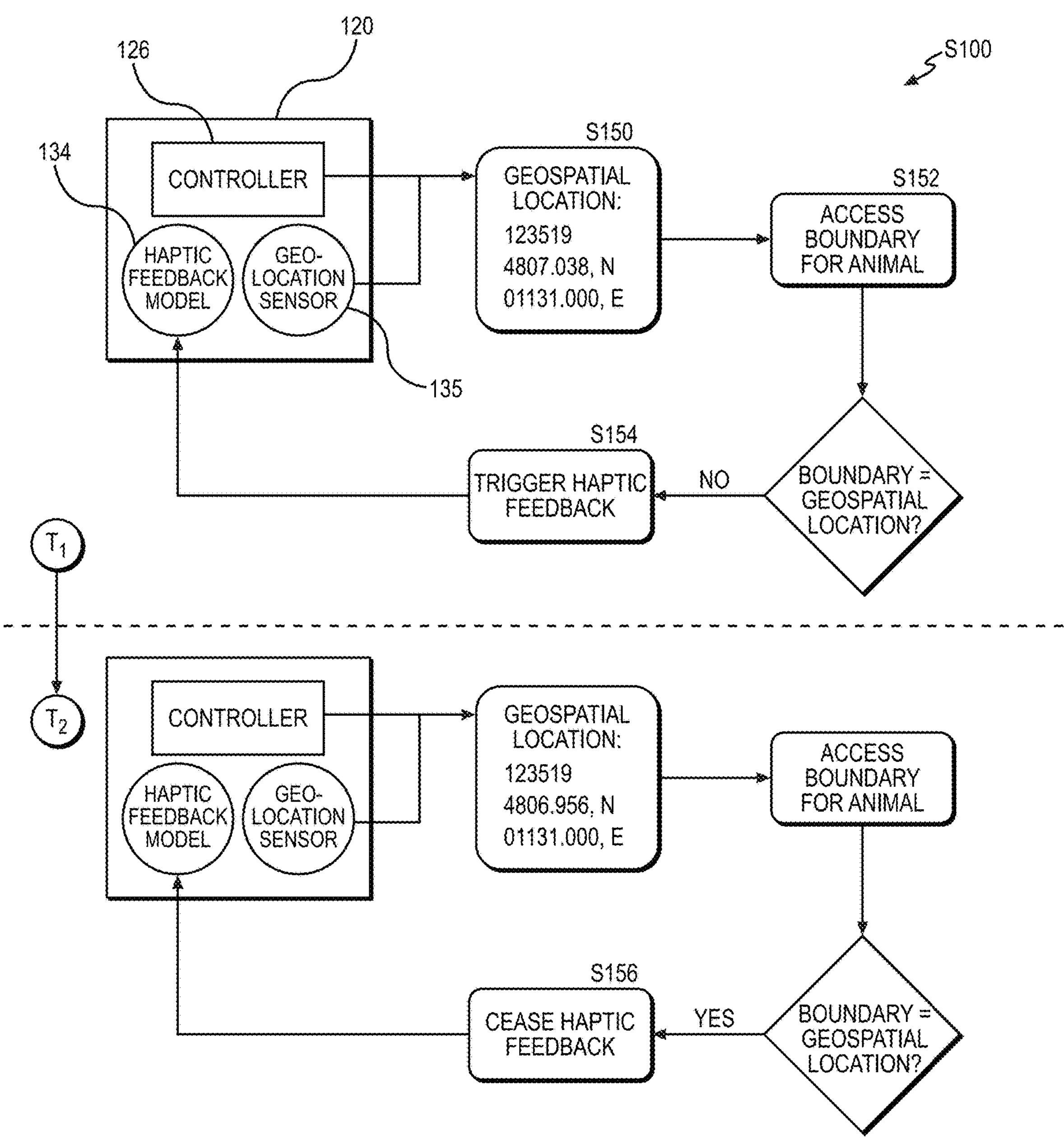
FIG. 4 is a flowchart representation of one variation of the method.
Figure 5:
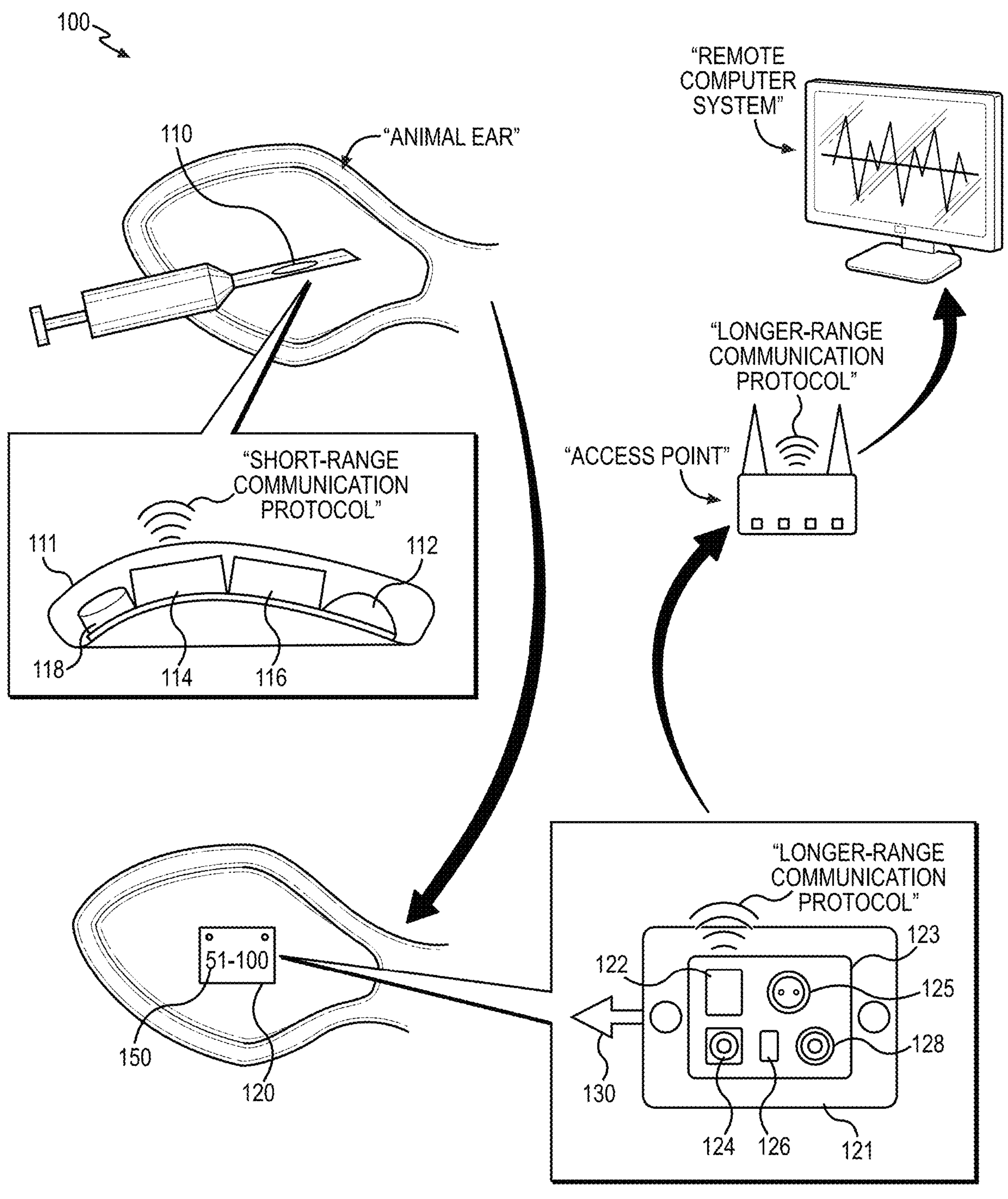
FIG. 5 is a schematic representation of one variation of the system.
Figure 6:
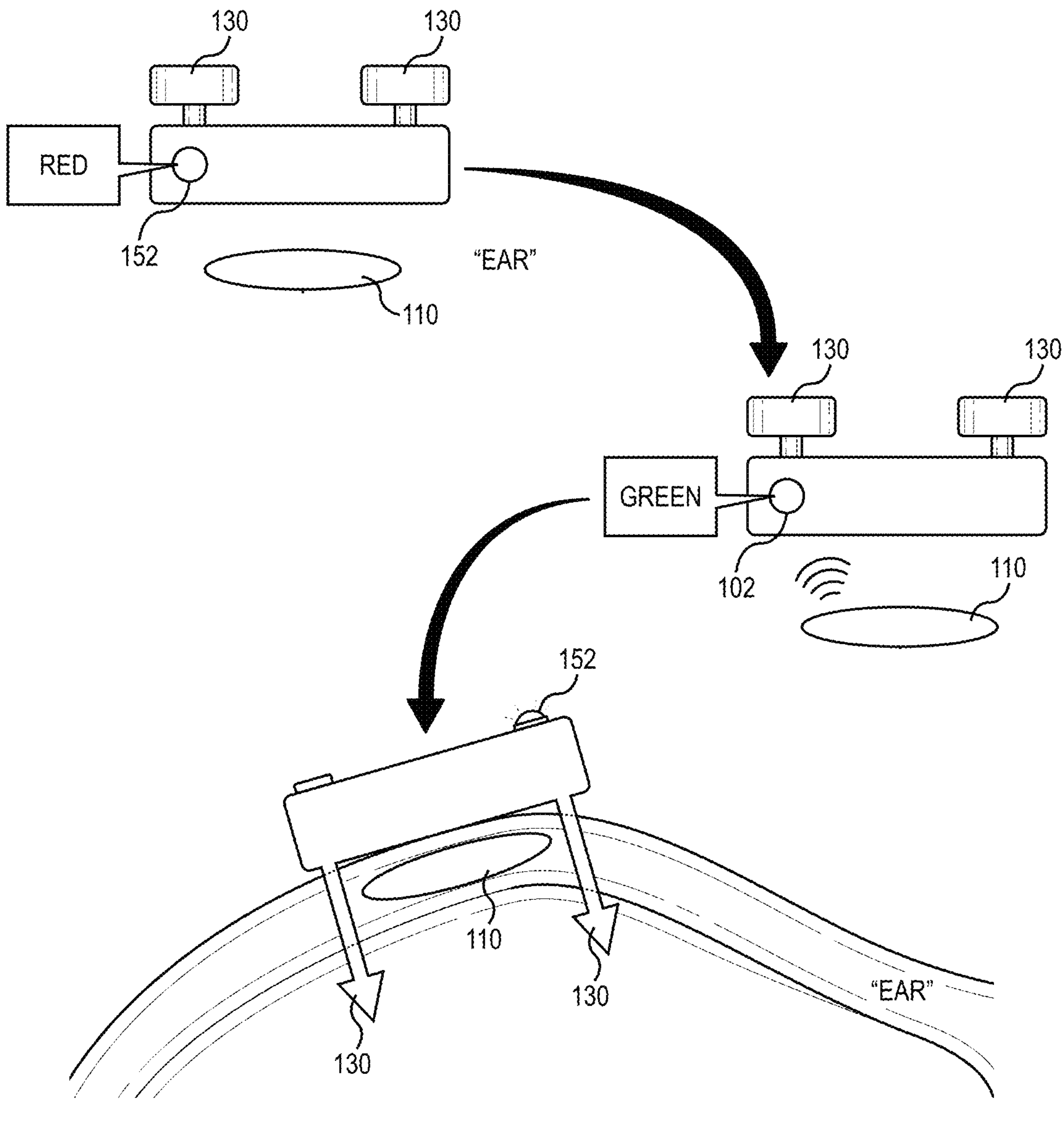
FIG. 6 is a schematic representation of one variation of the system.
Figure 7:
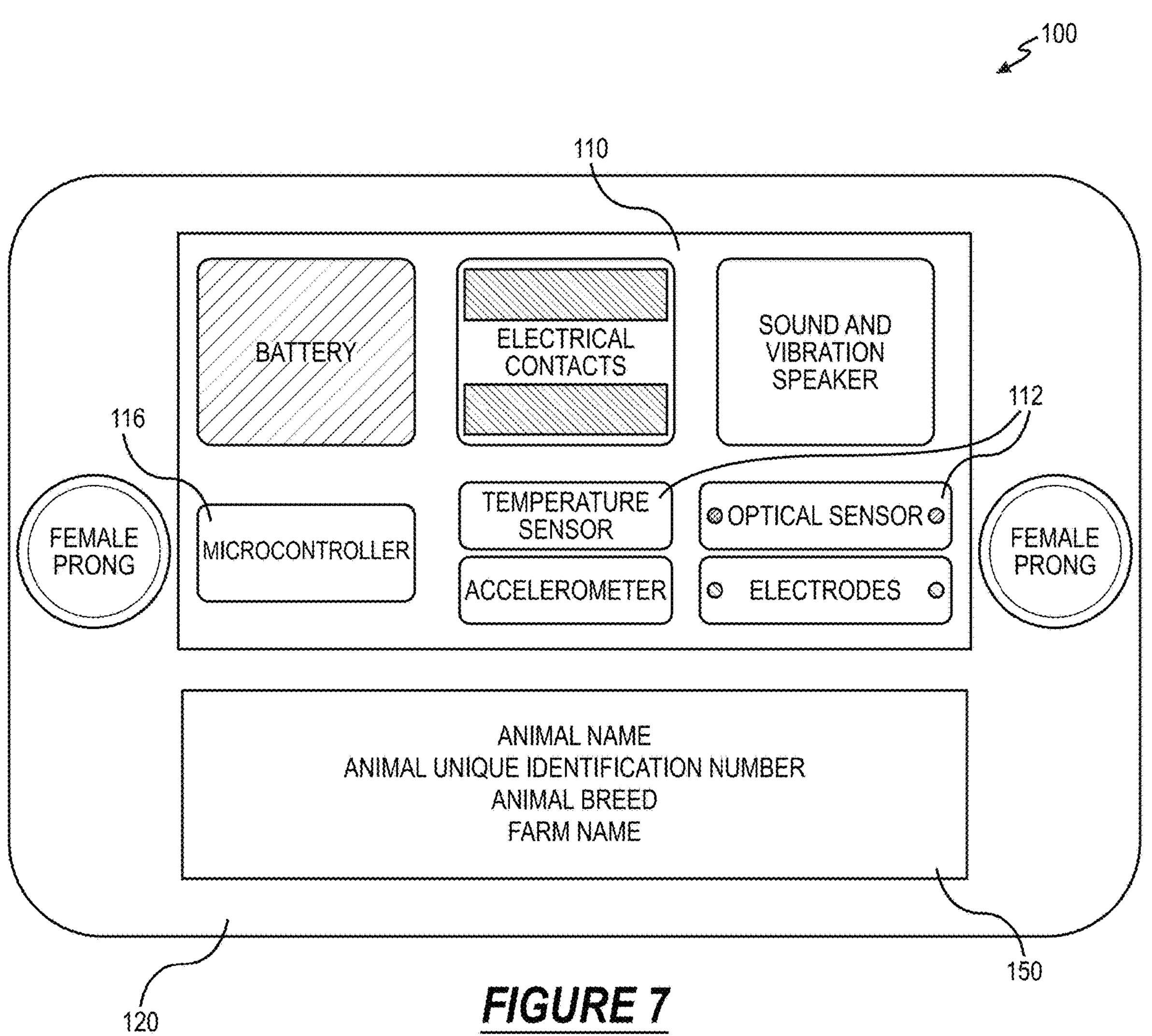
FIG. 7 is a schematic representation of one variation of the system.
Figure 8:
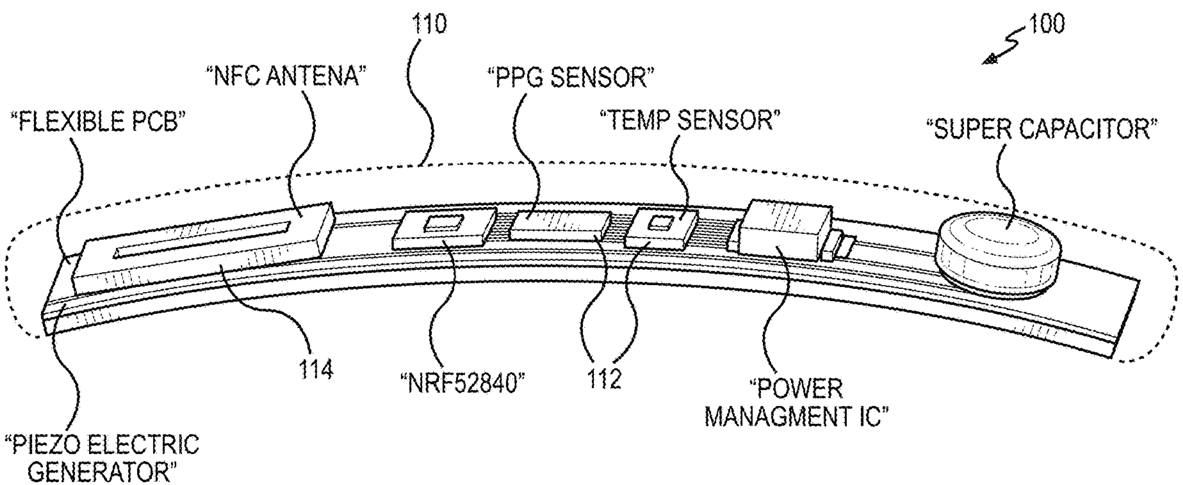
FIG. 8 is a schematic representation of one variation of the system.

As shown in FIGS. 3 and 4, a method S100 includes, at a superficial tag 120 located on an animal proximal a subdermal sensor unit 110 injected under skin of an animal: at a first time, triggering an inductive charging cell 128 of the superficial tag 120 to supply power from a battery 125 in the superficial tag 120 to an inductive charging coil 118 of a subdermal sensor unit 110 during a first time window in Block S112.

The method S100 further includes, at the subdermal sensor unit 110, in response to receiving power from the superficial tag 120 via the inductive charging coil 118: entering an active state; capturing a set of biometric data from an optical biometric sensor arranged within the subdermal sensor unit 110 during the first time window in Block S120; capturing an internal temperature of the animal from a temperature sensor arranged within the subdermal sensor unit 110 during the first time window in Block S120; generating a set of data packets representing the set of biometric data and the internal temperature of the animal and including a unique identifier associated with the subdermal sensor unit 110 in Block S122; and, via a subdermal short-range wireless transmitter 114 located within the subdermal sensor unit 110, broadcasting the set of data packets at a first power level via a short-range wireless communication protocol in Block S124.

The method S100 further includes, at the superficial tag 120: at a wireless communication module 122, intercepting the set of data packets based on the short-range wireless communication protocol in Block S130; and transmitting the set of data packets to an access point at a second power level, greater than the first power level, via a long-range wireless communication protocol in Block S132.

2. Applications

Generally, a system 100 includes a subdermal sensor unit 110 and a superficial tag 120 that cooperate to: collect subdermal biometric data—such as heart rate, breathing rate, dissolved blood oxygen, blood pressure, and subdermal temperature—from an animal (e.g., a domesticated bovid ungulates, "cow") over time (e.g., over one-minute intervals every hour of every day for one year); and to wirelessly transmit these subdermal biometric data to an access point. A computer system (e.g., a computer network, a computer server) can then: collect and aggregate these subdermal biometric data over time; monitor estrus (e.g., reproductive heath, "heat") and track health changes of the cow based on these subdermal biometric data; and serve specific and actionable directives to a cattle rancher, farmer, farm hand, or veterinarian accordingly, thereby enabling the cattle rancher, etc. to deploy limited resources effectively and when needed to directly support, maintain, and improve cattle health across a herd.

In particular, the subdermal sensor unit 110, injectable under skin of an animal, can include: a subdermal housing 111; a biometric sensor 112 configured to capture biometric data from under skin of the animal; and a subdermal short-range wireless transmitter 114 configured to broadcast this biometric data across a short transmission range (e.g., less than one inch) according to a short-range wireless communication protocol. The superficial tag 120, located within the short transmission range of the subdermal short-range wireless transmitter 114, can include a wireless communication module 122 configured to: intercept this biometric data broadcast by the subdermal short-range wireless transmitter 114 of the subdermal sensor unit 110; and transmit (or broadcast) this biometric data to a remote access point across a longer transmission range (e.g., up to one mile) according to a longer-range wireless communication protocol.

More specifically, a subdermal sensor unit 110 is injectable under skin of an ear of an animal, and a superficial tag 120 can install (e.g., via a set of barbs 130) on the ear of the animal directly over the subdermal sensor unit 110 such that: a short-range wireless receiver in the wireless communication module of the superficial tag is located directly over the subdermal short-range wireless transmitter, thereby minimizing distance between the tag receiver and subdermal transmitter, reducing transmit distance from the subdermal transmitter to the tag receiver; and reducing power consumption to transmit data from the subdermal transmitter to the tag receiver. In particular, minimizing a distance between the superficial tag receiver and the subdermal transmitter reduces path loss, to thereby enable the subdermal short-range wireless transmitter to define a lower transmit power for transmissions to the wireless receiver in the wireless communication module.

In one implementation, the subdermal sensor unit can receive (all) power from the superficial tag via wireless charging. Because wireless charging can be inefficient (e.g., 60-75% efficient), the subdermal short-range wireless transmitter defining the lower transmit power enables the superficial tag to store a lower amount of energy (e.g., 1.4 times less), to thereby enable the superficial tag to include a (smaller) battery (and/or operate over a longer period of time, more efficiently).

In particular, the subdermal sensor unit 110: captures biometric data; annotates these biometric data with a unique identifier of the subdermal sensor unit 110; transmits these biometric data, annotated with the unique identifier to the superficial tag (e.g., the superficial receiver within the wireless communication module of the superficial tag) over short-range, low-power wireless communication protocol, such as via a discrete short-range transmission antenna (e.g., NFC) in the subdermal sensor unit or via load modulation via the inductive charging coil while receiving an inductive charging signal from the superficial tag. The superficial tag: receives these data from the subdermal sensor unit 110; and passes these data to a remote access point, such as over longer-range, low-power wireless communication protocol via a discrete longer-range, higher-power transmission antenna without initiation by an interrogation signal.

Accordingly, by automatically collecting biometric data from the cow and passing these data from the subdermal sensor unit 110 to the superficial tag 120 to the remote computer system, the system 100 can: automatically monitor health statuses of individual cows without need to corral the cows or otherwise manually handle the cows; collect more accurate and authentic biometric data that represent normal resting and normal activity of a cow, such as without additional bovine stress due to manual handling; and collect biometric data more consistently and at a higher frequency, such as one minute of every hour of every day.

Therefore, the system 100 can enable more accurate and complete representation of biometric data in an individual cow over time, and thus changes in these biometric data may more accurately predict or indicate changes in health status of an individual cow.

In particular, the system 100 can detect, interpret, and prompt action more accurately to thereby enable more efficient and effective deployment of resources to cows that need attention, thereby improving health outcomes and yield (e.g., meat, milk, offspring) via lower total consumption of resources (e.g., veterinarian time, antibiotics, manual labor) across a herd of cows.

For example, the system 100 can enable biometric data collection, transmission, and/or interpretation for a set (or herd) of animals while these animals are ranging over a space (e.g., territory, pasture, field) without corralling the set of animals into a local area (e.g., paddock) and without manually extracting these data (e.g., via an interrogation signal) from the subdermal sensor unit 110 and/or the superficial tag 120.

2.1 Subdermal Wireless Charging and Decoupled Data Transmission

In one implementation, the subdermal sensor unit 110 includes: a local energy store (e.g., battery, capacitor) sized to power the subdermal sensor unit for a brief time period (e.g., up to ten minutes); an inductive charging coil; and a short-range transmission antenna distinct from the inductive charging coil.

In this implementation, the superficial tag includes: a battery (e.g., a coin cell battery) configured to store sufficient energy to power the subdermal sensor unit and superficial tag for a longer time period (e.g., six months, two years); an inductive charging cell configured to locate over the inductive charging coil in the subdermal sensor unit when the superficial tag is installed on an ear over the subdermal sensor unit located under the skin of the ear; and a short-range receiving antenna distinct from the inductive charging cell.

In this implementation, the superficial tag can send power to the subdermal sensor unit. In particular, the subdermal sensor unit can include an inductive charging coil configured to charge a local energy store (e.g., a battery) with power received from the superficial tag. In particular, once the local energy store of the subdermal sensor unit reaches a sufficient voltage, the subdermal sensor unit can enter an active state, capture biometric data, and transmit these biometric data to the superficial tag via the subdermal short-range receiving antenna.

Accordingly, the subdermal sensor unit 110 can characterize a low-power profile such that a power provided by the superficial tag 120 approximates a power threshold, defined by power required to activate and capture data by the biometric sensor 112 and power required to broadcast data packets, including these data captured by the biometric sensor 112 and a unique identifier associated with the subdermal sensor unit 110, across a broadcast range defined by the short-range wireless communication protocol.

2.2 Subdermal Wireless Charging and Decoupled Data Transmission via Load Modulation Alternatively, the subdermal sensor unit 110 can exclude a short-range transmission antenna and the superficial tag 120 can exclude a short-range receiving antenna. In this variation, the subdermal sensor unit can: at a first time, store a first set of biometric data, collected during a first biometric data collection cycle, within a local memory of the subdermal sensor unit; at a second time succeeding the first time, receive power from the superficial tag (e.g., via the inductive charging coil) to power a second biometric data collection cycle; and, at the second time, transmit (or otherwise broadcast) the first set of biometric data (and/or any biometric data stored in the local memory, i.e., from last data collection period) to the superficial tag via load modulation.

2.3 Subdermal Wireless Charging and Coupled Data Transmission via Load Modulation Alternatively, the subdermal sensor unit 110 can exclude a short-range transmission antenna and a local energy store, and the superficial tag 120 can exclude a short-range receiving antenna. Accordingly, the superficial tag 120 can transmit power to the subdermal sensor unit in real time to prompt the subdermal sensor unit to sample biometric data and stream these biometric data to the superficial tag 120 via an inductive charging coil.

In particular, the subdermal sensor unit 110 can: transmit the unique identifier to the superficial tag 120 via load modulation; capture a set of biometric data; and stream the set of biometric data to the superficial tag 120 via load modulation.

Accordingly, in this variation, the subdermal sensor unit 110 can stream biometric data to the superficial tag 120 without data latency between data capture and data streaming (or transmitting). Additionally, the subdermal sensor unit 110 can define a low-energy profile by capturing only biometric data while the superficial tag 120 is providing power to the subdermal sensor unit 110.

2.4 Installation

In particular, the subdermal sensor unit 110 and the superficial tag 120 can wirelessly communicate—via the subdermal short-range wireless transmitter 114 and the tag wireless communication module 122—based on proximity between the subdermal sensor unit 110 and superficial tag 120.

Because the subdermal short-range wireless transmitter 114 can be configured to broadcast data at a first power (e.g., nine mW, three mW) according to a short-range wireless communication protocol (e.g., near-field communications), the system 100 can enable passive offload of data from the subdermal sensor unit 110 without initiation by an interreference signal (e.g., radio frequency identification). Additionally, because the tag wireless communication module 122 can be configured to broadcast data at a second power (e.g., 20 mW) according to a longer-range wireless communication protocol, the system 100 can enable passing offload of data from the superficial tag 120 without initiation by an interreference signal (e.g., radio frequency identification).

Additionally, the tag wireless communication module 122 can intercept data broadcast by the subdermal short-range wireless transmitter 114 based on proximity between the subdermal sensor unit 110 and the superficial tag 120. In particular, the superficial tag 120 can include a set of barbs 130 configured to pass through an ear of the animal to retain the tag housing 121 on the ear of the animal and maintain proximity between the subdermal short-range wireless transmitter 114 and the tag wireless communication module 122. In particular, during installation of the system 100 on an animal, a user may: inject the subdermal sensor unit 110 under skin of an ear of an animal to install the subdermal sensor unit 110 subdermally within the ear of the animal; and pass the set of barbs 130 through the ear of the animal proximal an injection site of the subdermal sensor unit 110 such that the set of barbs 130 axially straddle the subdermal sensor unit 110 to prevent migration of the subdermal sensor unit 110 within skin (or the ear) of the animal.

Accordingly, the set of barbs 130 can retain a position of the superficial tag 120 on the ear of the animal—proximal the injection site of the subdermal sensor unit 110—to thereby maintain wireless communication between the subdermal short-range wireless transmitter 114 and the tag wireless communication module 122 according to the short-range wireless communication protocol defined by the subdermal sensor unit 110.

Therefore, the subdermal transmitter and the superficial receiver (and/or the inductive charging coil and the inductive charging cell) can be installed within a particular distance relative to each other to: improve energy efficiency; reduce a size of the subdermal sensor unit and/or the superficial tag; improve animal comfort while the superficial tag and subdermal sensor unit are installed within and upon the animal; and inherently secure data transmission between the subdermal sensor unit and the superficial tag.

The system 100 is described herein as including a set of barbs 130 configured to pass through an ear of the animal to retain the tag housing 121 on the ear of the animal and maintain proximity between the subdermal short-range wireless transmitter 114 and the tag wireless communication module 122. However, the superficial tag 120 can include any other retention forms, such as a spring element 132 configured to bias a tag housing 121 toward the ear of the animal, a single barb configured to partially pass through skin of the animal, etc.

2.5 Data Collection Triggers

In one implementation the superficial tag can: access a sampling schedule; and, according to the sampling schedule, transmit power to the subdermal sensor unit to trigger the subdermal sensor unit to collect a set of biometric data. The subdermal sensor unit can then: receive power from the superficial tag to recharge an internal energy storage of the subdermal sensor unit; collect the set of biometric data over a sampling window (e.g., ten minutes) according to the sampling schedule (e.g., an internal sampling schedule, the sampling schedule of the superficial tag); store the set of biometric data in a local memory unit of the subdermal sensor unit; and broadcast the set of biometric data to the superficial tag via a subdermal short-range wireless transmitter 114 after the inductive charging cell—of the superficial tag—ceases power supply to the inductive charging coil of the subdermal sensor unit.

Additionally or alternatively, the superficial tag 120 can transmit power to the subdermal sensor unit 110 to prompt the subdermal sensor unit 110 to enter an active state and begin data collection (e.g., biometric data collection). Additionally or alternatively, the superficial tag 120 can prompt the subdermal sensor unit 110 to collect a particular set of biometric data (e.g., heart rate). In this variation, the superficial tag 120 can transmit the prompt to the subdermal sensor unit 110 via an inductive charging coil via amplitude (or frequency) modulation or via a short-range wireless transmitter in the tag wireless communication module.

2.6 Virtual Fencing

In one variation, the superficial tag 120 further includes: a geospatial sensor; and a feedback module 134 configured to output haptic, audible, and/or electric-shock feedback responsive to the animal approaching or passing a geospatial boundary.

In particular, the superficial tag 120 further includes a controller configured to: access a geospatial boundary, such as assigned to the herd generally or cow specifically and stored in local memory; access a current location from the geospatial sensor; and trigger a feedback module 134 responsive to the current location falling within a threshold distance—or outside of—the geospatial boundary.

2.7 Disclaimers

Blocks of the method S100 are described herein as executed by a remote computer system (e.g., a remote server, hereinafter a "computer system"). However, Blocks of the method S100 can be executed by one or more entities accessing the network, by a local computer system, or by any other computer system-hereinafter a "system."

The system and method are described herein for one instance of one animal. However, one instance of the system can be installed on many or every animal (e.g., cows) in a herd to track biometrics, motion, location, and/or environmental exposure, etc. of these individual animals over time.

3. Subdermal Sensor Unit

Generally, the system 100 includes a subdermal sensor unit 110: injectable under skin of an animal; and configured to collect biometric data from the animal and transmit this biometric data to a superficial tag 120 located proximal the subdermal sensor unit 110.

In particular, the subdermal sensor unit 110 can include: a subdermal housing 111 encasing components of the subdermal sensor unit 110; a biometric sensor 112 (or a set of biometric sensors) configured to capture biometric data (e.g., optical data, electrical data, temperature data, activity data); and a subdermal short-range wireless transmitter 114 configured to execute local transmission of data captured by the subdermal sensor unit 110 via a short-range wireless communication protocol (e.g., near-field communications).

3.1 Biometric Sensor

Generally, the subdermal sensor unit 110 includes a biometric sensor 112 configured to capture biometric data from under the skin of the animal. In particular, the subdermal sensor unit 110 can include: an optical sensor configured to capture optical data (e.g., blood color, blood flow volume, venous return, light waveforms) from under the skin of the animal; and a temperature sensor configured to capture internal temperature data from under the skin of the animal. More specifically, the subdermal sensor unit 110 can include: a temperature sensor configured to read an internal temperature of the animal; an optical biometric sensor 112 configured to collect a set of optical data from the ear of the animal; and a controller 116. In this implementation, the controller 116 of the subdermal sensor unit 110 can: read a set of temperature values, indicating the internal temperature of the animal during a sampling period, from the temperature sensor; read the set of optical data from the biometric sensor 112 during a sampling period; and calculate a set of biometric values (e.g., blood oximetry, blood pressure, heart rate, breathing rate) based on the set of optical data. In one example, the biometric sensors 112 of the subdermal sensor unit 110 can capture optical data of blood flow from under skin of an animal. In one variation, the biometric sensor 112 arranged within the subdermal sensor unit 110 includes a geospatial location sensor 135 configured to capture a geospatial location and/or a series of geospatial locations of the animal.

3.2 Subdermal Wireless Transmitter

Generally, the subdermal sensor unit 110 includes a subdermal short-range wireless transmitter 114 configured to transmit data collected by the set of biometric sensors to a superficial tag 120 located proximal the subdermal sensor unit 110. In one implementation, the subdermal short-range wireless transmitter 114 can: access a set of biometric values and a set of temperature values captured by the biometric sensor 112 during a sampling period; and transmit the set of biometric values, the set of temperature values, and a unique identifier associated with the subdermal sensor unit 110 to a wireless communication module 122 of a superficial tag 120—proximal the subdermal sensor unit 110—following conclusion of the sampling period.

In particular, the subdermal short-range wireless transmitter 114 is configured to broadcast a set of biometric data captured by the biometric sensor 112 at a first power level via a short-range wireless communication protocol. For example, the subdermal short-range wireless transmitter 114 can: access a set of biometric data captured by the biometric sensor 112; and broadcast the set of biometric data at a first power level (e.g., 1 mW, 10 mW) via near-field communications, such as over a distance of one and a half inches. Additionally or alternatively, the subdermal short-range wireless transmitter 114 can: access a set of biometric data captured by the biometric sensor 112; and broadcast the set of biometric data at a first power level via near-field communications, such as over a range of one-half to two inches. Additionally or alternatively, the subdermal short-range wireless transmitter 114 can: access a set of biometric data captured by the biometric sensor 112; and broadcast the set of biometric data at a first power level via inductive coupling (e.g., near-field inductive communication), such as via magnetic field coupling over a range of one-half to three inches. Additionally or alternatively, the subdermal short-range wireless transmitter 114 can: access a set of biometric data captured by the biometric sensor 112; and broadcast the set of biometric data at a first power level via a short-range radio frequency protocol (e.g., personal area network protocol) such as over a range of one-half to two inches.

Accordingly, the subdermal sensor unit 110 can transmit data to (and/or receive data from) a superficial tag 120 located proximal the subdermal sensor unit 110 via short-form communication protocols to thereby limit the power consumption of transmission of these biometric data collected by the subdermal sensor unit 110.

Additionally, the subdermal sensor unit 110 is associated with a unique identifier representative of the subdermal sensor unit 110. In particular, when the subdermal short-range wireless transmitter 114 broadcasts data (e.g., biometric data), the subdermal short-range wireless transmitter 114 can include the unique identifier in this broadcasted data such that a wireless communication module 122 intercepting and/or receiving the set of data can identify the subdermal sensor unit 110 as an origin of the set of data, and therefore identify an animal associated with the subdermal sensor unit 110.

3.3 Inductive Charing Coil+Power

In one implementation, the subdermal sensor unit 110 includes an inductive charging coil 118 configured to receive energy from an inductive charging cell 128 external to the subdermal sensor unit 110 (e.g., located on/within a superficial tag 120 proximal the subdermal sensor unit 110). In particular, the subdermal sensor unit 110 includes an inductive charging coil 118. In this implementation, the subdermal sensor unit 110 is configured to: activate upon receiving power from the battery 125 via the inductive charging coil 118; capture the set of biometric data, via the biometric sensor, upon activation; and transmit the set of biometric data to the superficial tag 120 prior to completion of the sampling period.

Accordingly, the subdermal sensor unit 110 can include: a biometric sensor 112 configured to collect biometric data from under skin of an animal; and a subdermal short-range wireless transmitter 114 configured to transmit data collected by the biometric sensor 112 according to a low-power- and therefore short-range-communication protocol.

3.4 Subdermal Sensor Unit Housing

Generally, the subdermal sensor unit 110 includes a subdermal sensor unit housing 111 encasing components of the subdermal sensor unit 110. In one implementation, the subdermal sensor unit housing 111 can define an ellipsoid volume. In particular, the subdermal sensor unit housing 111 can define a bullet (or "lozenge") geometry (e.g., 47 mm by 4 mm by 7 mm). In this implementation, the subdermal sensor unit 110 is implantable via a six-gauge hypodermic needle. In particular, in this implementation, the subdermal sensor unit housing 111 can: include a polymer encasing the biometric sensor 112 and the subdermal short-range wireless transmitter 114; and define a lozenge geometry characterized by a width less than 5/32 of an inch. In this implementation, the subdermal sensor unit 110 is configured to inject under the skin of the animal via a six-gauge hypodermic needle.

Additionally or alternatively, the subdermal sensor unit 110: defines a lozenge geometry characterized by a width less than 15/64 of an inch; and is configured to inject under the skin of the animal via a four-gauge hypodermic needle.

Additionally or alternatively, the subdermal sensor unit 110: defines a lozenge geometry characterized by a width less than 5/64 of an inch; and is configured to inject under the skin of the animal via a fourteen-gauge hypodermic needle.

In one implementation, the subdermal sensor unit housing 111 defines a biocompatible polymer (e.g., silicon, non-toxic polydimethylsiloxane). In particular, the subdermal sensor unit housing 111 can encase a biometric sensor, an inductive charging coil, and a subdermal short-range transmission unit (e.g., antenna), such as by overmolding with a biocompatible polymer. In one variation, the subdermal sensor unit 110 includes a flexible printed circuit board (or "PCB"). In this variation, the subdermal sensor unit 110: includes a flexible printed circuit board (or "PCB") encased within the subdermal sensor unit housing 111; a biometric sensor 112 arranged on the flexible printed circuit board; and a subdermal short-range wireless transmitter 114 arranged on the flexible printed circuit board.

4. Superficial Tag

Generally, the system 100 includes a superficial tag 120 configured to: install on the skin of an animal (e.g., supradermally) proximal the subdermal sensor unit 110; receive data transmissions from the subdermal sensor unit 110; and transmit these data transmissions to a remote access point (e.g., in a barn, via a mobile device). In particular, the superficial tag 120 includes: a tag housing 121; and a wireless communication module 122. The tag wireless communication module 122 is located within the tag housing 121 and configured to: receive the set of biometric data broadcast by the subdermal short-range wireless transmitter 114 in the subdermal sensor unit 110; and transmit the set of biometric data to an access point at a second power level, greater than the first power level, via a longer-range wireless communication protocol.

4.1 Tag Wireless Communication Module: Short-Range Receiver and Long-Range Transmitter Generally, the superficial tag 120 includes a wireless communication module 122 configured to receive data packets broadcast from the subdermal sensor unit 110 and transmit (or broadcast) these data packets to a remote access point. In particular, the tag wireless communication module 122: is located within a particular range of the subdermal short-range wireless transmitter 114 of the subdermal sensor unit 110; and configured to transmit data received from the subdermal sensor unit 110 via a longer-range communication protocol (e.g., Wide Area Network protocol, LTE-M, cellular protocol) configured to transmit data over a particular range (e.g., one mile, five miles). In particular, the tag wireless communication module 122 is configured to transmit over long range without initiation from an interrogation signal.

In one variation, the superficial tag 120 includes: the tag wireless communication module 122 configured to transmit the set of biometric data and a first identifier, associated with the subdermal sensor unit 110, to the access point; a radio frequency identification chip 150 arranged within the superficial tag 120 and configured to broadcast a second identifier, associated with the superficial tag 120, in response to receipt of an interrogation signal; and the tag housing 121 depicting a third visual identifier associated with the animal.

4.2 Construction

In one implementation, the superficial tag 120 includes: a flexible printed circuit board configured to elastically bend with the ear of the animal; the tag housing 121 encasing the flexible (or rigid) printed circuit board; and the tag wireless communication module 122 arranged on the flexible printed circuit board. In one example, the superficial tag 120 includes a tag housing 121: defining a rectangular geometry (e.g., 13/16 inches wide); and formed of a thermoplastic polyurethane.

4.3 Sensors

In one implementation, the superficial tag 120 includes: an ambient temperature sensor configured to collect environmental data (e.g., ambient temperature, humidity data, air quality); and a geospatial location sensor 135 configured to collect geospatial location data of the animal. In particular, in the foregoing implementation, the superficial tag 120 includes: an ambient sensor 124 configured to collect a set of ambient data from an environment external the animal during the sampling period; and a geospatial location sensor 135 configured to collect a geospatial location of the animal during the sampling period.

In one example, the superficial tag 120 can include a geospatial location sensor 135 configured to capture a series of geospatial locations of the animal during a sampling and/or target time period. Additionally or alternatively, the superficial tag 120 can include a geospatial location sensor 135 configured to selectively record a geospatial location of the animal in response to detecting a particular condition (e.g., weather condition, proximity to a boundary, proximity to another animal).

In particular, in the foregoing implementation, the superficial tag 120 is configured to: receive a set of biometric values captured during a sampling period, a set of temperature values captured during the sampling period, and a unique identifier from the subdermal sensor unit 110 via the tag wireless communication module 122 of the superficial tag 120; pair the set of biometric values and the set of temperature values with the set of ambient data and the geospatial location based on the sampling period; and transmit the set of biometric values, the set of temperature values, the set of ambient data, the geospatial location of the animal, and a unique identifier to the access point.

In one variation, the superficial tag 120 includes an external sensor (e.g., an accelerometer) configured to capture external data (e.g., accelerometer data, position data) at a particular sampling rate (e.g., ten Hz, 30 Hz), such as during a sampling period.

Accordingly, in the foregoing implementations, the superficial tag 120 can include a set of environmental sensors to collect ambient data to thereby augment (e.g., contextualize) data captured by the subdermal sensor unit 110.

4.4 Inductive Charging

In one implementation, the superficial tag 120 includes an inductive charging cell 128 configured to inductively transmit power to an inductive charging coil 118 of a subdermal sensor unit 110 proximal the superficial tag 120. In particular, the superficial tag 120 can include a battery 125; and an inductive charging cell 128 configured to transmit power from the battery 125 to the inductive charging coil 118 of the subdermal sensor unit 110. For example, the superficial tag 120 can include a battery 125 (e.g., a coin cell battery 125) configured to sustain power for a particular time period (e.g., one year, two years), and be manually replaceable by a user. In another example, the superficial tag 120 can include: a set of solar cells configured to collect ambient solar energy; a capacitor (and/or battery 125) configured to store energy collected by the set of solar cells; and an inductive charging cell 128 configured to transmit power from the battery 125 to the inductive charging coil 118 of the subdermal sensor unit 110.

4.4.1 Data Transmission Via Inductive Charging Components

In one variation, the superficial tag can: exclude a wireless communication module and/or a short-range wireless receiver; and include an inductive charging cell. In this variation, the superficial tag can: transmit power from the superficial tag via the inductive charging cell of the superficial tag and the inductive charging coil of the subdermal sensor unit; enable the subdermal sensor unit to enter an active state; and, while the superficial tag is powering the subdermal sensor unit via the inductive charging cell, receive a set of biometric data via load modulation by the subdermal sensor unit.

For example, the superficial tag can receive modulated data (e.g., based on amplitude, frequency, phase of electromagnetic field) representing the set of biometric data collected by the subdermal sensor unit; interpret the modulated data (e.g., controls signals, status signals) as the set of biometric data; and transmit the set of biometric data to the access point via a long-range wireless communication transmission antenna.

Accordingly, the superficial tag can define a minimum amount of components—such as an inductive charging cell configured to transmit power and receive data to and from the subdermal sensor unit—to thereby decrease weight of the superficial tag and increase comfort for an animal retaining the superficial tag.

4.5 Energy Harvesting

In one variation, the superficial tag 120 includes: a piezoelectric transduction unit configured to convert movement of the animal into electrical energy; and an inductive charging cell 128 configured to transmit power from the piezoelectric transduction unit to the inductive charging coil 118 of the subdermal sensor unit 110. In particular, in this variation, the superficial tag 120: is located on an ear of an animal; and includes a piezoelectric transduction unit configured to convert mechanical ear movements of the ear of the animal into electrical energy.

Accordingly, the superficial tag 120 can: install on skin of an animal proximal (e.g., within a threshold distance of) a subdermal sensor unit 110 injected into skin of the animal; include a wireless communication module 122 configured to receive short-range communications from the subdermal sensor unit 110 and transmit long-range communications to a remote access point; and/or include a power source configured to inductively power the subdermal sensor unit 110.

4.6 Barbs and Installation

Generally, the superficial tag 120 includes a set of barbs 130: arranged on a distal end of the superficial tag 120; and configured to install through skin of the animal and retain proximity between the subdermal sensor unit 110 and the superficial tag 120 to maintain wireless communication between the subdermal short-range wireless transmitter 114 and the tag wireless communication module 122 of the superficial tag 120. In particular, the set of barbs 130 includes: a first barb; and a second barb laterally offset from the first barb at a second length greater than a first length of the subdermal sensor unit 110. The set of barbs 130 is configured to: straddle the proximal end of the subdermal sensor unit 110 and the distal end of the subdermal sensor unit 110; and retain a position of the subdermal sensor unit 110, coaxial to the superficial tag 120, to limit axial migration of the subdermal sensor unit 110 within the ear of the animal. Accordingly, the superficial tag 120 can include a set of barbs 130 configured to retain the position of the subdermal sensor unit 110 within the ear of the animal.

In particular, the set of barbs 130 can be configured to locate the tag wireless communication module 122 over the subdermal short-range wireless transmitter 114 to maintain wireless connectivity between the subdermal short-range wireless transmitter 114 and the tag wireless communication module 122. For example, each barb in the set of barbs 130 can include a distal end defining a conical tapered geometry and a reverse-angled projection. Additionally or alternatively, in another example, the set of barbs 130 can define: a tissue-conforming profile such that a distal end of each barb in the set of barbs 130 is configured to elastically compress during insertion of the barb into the skin of the animal and elastically expand (e.g., on a distal end of the ear of the animal) to retain insertion of these barbs in an ear of the animal.

In one implementation, the superficial tag includes a backing plate configured to: receive the set of barbs on a back side of the ear of the animal; and retain the superficial tag on the ear of the animal. In particular, the backing plate can define a set of laterally offset apertures configured to receive the set of barbs of the superficial tag.

In this implementation, the set of barbs can insert through the set of laterally offset apertures to transiently retain the superficial tag to the backing plate, and thereby retain the superficial tag on the ear of the animal. For example, the superficial tag can install on a first side (e.g., a face) of an ear of the animal via insertion of the set of barbs through the ear of the animal, and the backing plate can locate on a second side (e.g., back of the ear of the animal) opposite the first side. The set of barbs can then insert through the set of laterally offset apertures.

5. Installation

Generally, the subdermal sensor unit 110 can be injected under skin of an ear of an animal, and the superficial tag 120 can locate on skin of the animal proximal the subdermal sensor unit 110. In particular, the subdermal sensor unit 110 can be injected under skin of an animal via a hypodermic needle of an application device, and the superficial tag 120 can be installed over skin of the animal and proximal (e.g., overlaid on, laterally offset from, coaxial with) the subdermal sensor unit 110.

In one example, the subdermal sensor unit 110 can: be loaded into an injector (e.g., six-gauge hypodermic needle); and be injected under skin of the ear of the animal. Then, the superficial tag 120 can be installed over the subdermal sensor unit 110 to align the receiver of the superficial tag 120 with the transmitter of the subdermal sensor unit 110 and/or the inductive charging coil of the subdermal sensor unit and the inductive charging cell of the superficial tag.

In one implementation, the superficial tag 120 includes a set of barbs 130 (e.g., a pair of barbs): coupled to the tag housing 121; and configured to retain the tag housing 121 to the ear of the animal.

In another implementation, the set of barbs 130 can define an elastic material. In this implementation, an end of each barb in the set of barbs 130 can expand to retain the superficial tag 120 on the ear of the animal once the set of barbs 130 passes through the ear of the animal.

In particular, the superficial tag can define a set of apertures (e.g., holes, bores, receptacles). In one example, the superficial tag 120 can, during an unloaded state, include the set of barbs 130 retracted into the superficial tag 120 such that tips of the set of barbs 130 are enclosed within the superficial tag 120. Additionally or alternatively, the set of barbs 130 can transiently install on the superficial tag 120.

In this implementation, once the superficial tag 120 is located over the subdermal sensor unit 110 on the ear of the animal, the set of barbs 130 can inject through the set of apertures on the superficial tag and the ear of the animal. For example, an application (or other installation tool) can rapidly drive the set of barbs 130 through the ear of the animal.

In one variation the barbs can couple a backing plate located on a back of an ear of the animal. In another variation, the system 100 can include a set of buttons configured to install on a barb protruding from the back of the ear of the animal.

In yet another variation, the superficial tag 120 can include a first barb configured to retain the tag housing 121 to the ear of the animal and locate the tag wireless communication module 122 over the subdermal short-range wireless transmitter 114 to maintain wireless connectivity between the subdermal short-range wireless transmitter 114 and the tag wireless communication module 122.

5.1 Installation Feedback

In one implementation, the superficial tag 120 can include a light element 152 (e.g., an LED light) configured to activate in response to detection of proximity (e.g., within 4 inches) to the subdermal sensor unit 110. In particular, the superficial tag 120 can include a light element 152 and a controller 126 configured to, during installation of the system on an ear: read receipts of transmission confirmations from the tag wireless communication module 122; and, in response to detection of receipt of a first communication, from the subdermal short-range wireless transmitter 114 via the tag wireless communication module 122, trigger activation of the light element 152 to indicate proximity of the superficial tag 120 to the subdermal sensor unit 110. A user may then, upon activation of the light element 152 on the superficial tag 120, install the superficial tag 120 while the light element 152 is activated to confirm a location of installation for the superficial tag 120.

In one example, during installation of the system on an ear, the subdermal short-range wireless transmitter 114 can transmit a beacon signal (e.g., a constant beacon signal) after injection of the subdermal sensor unit 110 under the skin of the animal and while a user navigates a superficial tag 120 proximal an injection site of the subdermal sensor unit 110. The superficial tag 120 can: via the tag wireless communication module 122, detect the beacon signal; and, in response to detection of the beacon signal, activate a light element 152 located superficially on the superficial tag 120. In particular, in this example, the controller 126 of the superficial tag 120 can: define a threshold beacon signal strength (e.g., based on voltage or energy density of the beacon signal); in response to detection of a beacon signal of a first beacon signal strength falling below the threshold beacon signal strength, withhold activation of the light element 152; and, in response to detection of a second beacon signal of a second beacon signal strength exceeding the threshold beacon signal strength, activate the light element 152 to indicate proximity between the subdermal sensor unit 110 and the superficial tag 120 sufficient for low-power data communication between the subdermal sensor unit 110 and the superficial tag 120.

Additionally or alternatively, in another example, the superficial tag 120 can define a light element 152 configured to activate in a particular color, each color indicating an installation proximity to the subdermal sensor unit 110. In particular, in this example, the controller 126 of the superficial tag 120 can: in response to detecting absence of a beacon signal received by the tag wireless communication module 122, activate the light element 152 in a first color (e.g., red); in response to detection of a first beacon signal of a first beacon signal strength falling below the threshold beacon signal strength, activate the light element 152 in a second color (e.g., yellow); in response to detection of a second beacon signal of a second beacon signal strength exceeding the threshold beacon signal strength, activate the light element 152 in a third color (e.g., green) to indicate proximity between the subdermal sensor unit 110 and the superficial tag 120 sufficient for low-power data communication between the subdermal sensor unit 110 and the superficial tag 120; and prompt a user to install the superficial tag 120 while the light element 152 is activated in the third color.

In one variation, the subdermal sensor unit 110 defines a light element 152 configured to activate in response to detecting proximity of the superficial tag 120. In this variation, the subdermal sensor unit 110 includes a controller 116 configured to: during installation of the system on an ear, activate the light element 152 of the subdermal sensor unit 110 to enable a user to view an orientation and location of the subdermal sensor unit 110 under the skin of the animal. The user may then: orient the set of barbs 130 of the superficial tag 120 to the orientation and location of the subdermal sensor unit 110 and install the superficial tag 120 proximal the subdermal sensor unit 110 such that the set of barbs 130 straddle the subdermal sensor unit 110 according to the orientation of the subdermal sensor unit 110. In the foregoing variation, the set of barbs 130 of the superficial tag 120 can be aligned with a major axis of the subdermal sensor unit 110 to thereby prevent axial migration and/or drift of the subdermal sensor unit 110 and to maintain wireless connectivity between the superficial tag 120 and the subdermal sensor unit 110 based on proximity of the superficial tag 120 and the subdermal sensor unit 110.

6. Operation

Generally, the subdermal sensor unit 110 and the superficial tag 120 can cooperate to: capture a set of biometric data from under skin of an animal via biometric sensors arranged within the subdermal sensor unit 110; broadcast the set of biometric data—via low-power communication protocols—to a tag wireless communication module 122 proximal a subdermal short-range wireless transmitter 114; at the tag wireless communication module 122, intercept the set of biometric data; and, via the tag wireless communication module 122, transmit the set of biometric data—via higher-power communication protocols—to a remote access point.

6.1 Data Collection Triggers and Timing

In one implementation, the superficial tag can: access a sampling schedule; and, according to the sampling schedule, transmit energy (i.e., power) to the subdermal sensor unit to trigger the subdermal sensor unit to collect a set of biometric data. The subdermal sensor unit can then: receive energy from the superficial tag to recharge an internal energy storage of the subdermal sensor unit; collect the set of biometric data over a sampling window (e.g., ten minutes) according to the sampling schedule (e.g., an internal sampling schedule, the sampling schedule of the superficial tag); store the set of biometric data in a local memory unit of the subdermal sensor unit; and broadcast the set of biometric data to the superficial tag via a subdermal short-range wireless transmitter 114 after the inductive charging cell—of the superficial tag—ceases energy supply to the inductive charging coil of the subdermal sensor unit.

Accordingly, in the foregoing implementation, the subdermal sensor unit can selectively transmit data to the superficial tag in response to receiving energy from the superficial tag via a subdermal short-range wireless transmitter 114.

Additionally or alternatively, the subdermal sensor unit can: at a first time, receive energy from an inductive charging cell of the superficial tag to recharge a local energy store in the subdermal sensor unit; responsive to the local energy store exhibiting a charge level over a threshold charge level (e.g., 100%), collect the set of biometric data over a sampling window (e.g., ten minutes) according to the sampling schedule (e.g., an internal sampling schedule, the sampling schedule of the superficial tag); and store the set of biometric data in a local memory unit of the subdermal sensor unit. In this implementation, the subdermal sensor unit can, responsive to receiving energy from the inductive charging cell of the superficial tag at a second time, transmit the set of biometric data, from the local memory unit, to the superficial tag via load modulation.

In yet another implementation, the subdermal sensor unit can exclude a subdermal short-range wireless transmitter 114 and a local energy store, and include an inductive charging coil configured to: receive energy from an inductive charging cell of the superficial tag; and transmit (e.g., stream) biometric data, collected by the biometric sensor of the subdermal sensor unit, to the inductive charging cell of the superficial tag while the inductive charging cell is transmitting energy to the inductive charging coil via load modulation.

In another implementation, the superficial tag can access the sampling schedule and transmit the sampling schedule to the subdermal sensor unit. In particular, the subdermal sensor unit can implement the sampling schedule, such as: collecting a set of biometric data according to the sampling schedule; and transmitting the set of biometric data to the superficial tag via a subdermal short-range wireless transmitter 114 responsive to receiving energy from the superficial tag. In this implementation, the subdermal sensor unit can request energy from the superficial tag—when the local energy store is depleted (e.g., below a threshold charge level)—via the subdermal short-range wireless transmitter 114.

Additionally or alternatively, the subdermal sensor unit can: collect a set of biometric data according to the sampling schedule; and transmit the set of biometric data to the superficial tag via an inductive charging coil responsive to (e.g., while) receiving energy from the superficial tag. In this implementation, the subdermal sensor unit can request energy from the superficial tag—when the local energy store is depleted (e.g., below a threshold charge level)—via load modulation of the inductive charging coil.

In one variation, the superficial tag includes the inductive charging cell configured to transmit energy to the subdermal sensor unit by inducing a magnetic field between the inductive charging cell and the inductive charging coil. In this variation, the subdermal sensor unit includes: a local energy store configured to store energy received from the inductive charging cell, via the magnetic field, during a first time period; a local memory unit configured to store biometric sensor data captured by the biometric sensor during a second time period succeeding the first time period; and the inductive charging coil configured to transmit the set of biometric data, stored in the local memory unit, to the superficial tag via load modulation of the magnetic field during a third time period succeeding the second time period.

In this variation, the subdermal sensor unit can further be configured to store a sampling schedule in the local memory unit; based on the sampling schedule, transition from an inactive state to an active state during a first sampling interval within the second time period; capture a first set of biometric data during the first sampling interval; store the first set of biometric data in the local memory unit; return to the inactive state following the first sampling interval; based on the sampling schedule, transition from the inactive state to the active state during a second sampling interval within the second time period; capture a second set of biometric data during the second sampling interval; store the second set of biometric data in the local memory unit; return to the inactive state following the second sampling interval; and, responsive to receiving energy from the inductive charging cell of the superficial tag, transmit the first set of biometric data and the second set of biometric data from the local memory unit to the superficial tag.

Accordingly, in the foregoing implementations, the subdermal sensor unit and the superficial tag can exhibit a minimum count of parts and maintain efficient data transmission between the subdermal sensor unit 110 and the superficial tag 120.

6.2 Biometric Data Collection at the Subdermal Sensor Unit

Generally, the subdermal sensor unit 110 can capture a set of biometric data from under skin of the animal. In particular, the subdermal sensor unit 110 includes a biometric sensor 112 configured to: collect optical data representing blood movement and color of blood proximal the subdermal sensor unit 110 within the ear of the animal.

In one implementation, the subdermal sensor unit 110 includes a controller 116 configured to: access a sampling schedule defining sampling time windows and/or sampling time periods for the subdermal sensor unit 110 to capture biometric data; in response to detection of a first time period including a sampling time period defined by the sampling schedule, trigger the biometric sensor 112 to capture a set of biometric data from under skin of the animal; and, in response to detection of a second time period including a data transmission time period defined by the sampling schedule, trigger the subdermal short-range wireless transmitter 114 to broadcast the set of biometric data, captured by the biometric sensor 112 during the first time period.

Additionally or alternatively, the controller 116 of the subdermal sensor unit 110 can: access a sampling schedule defining sampling time windows and/or sampling time periods for the subdermal sensor unit 110 to capture biometric data; in response to detection of a first time period including a sampling time period defined by the sampling schedule, trigger the biometric sensor 112 to capture a set of biometric data from under skin of the animal; access a nominal set of biometric data representing a baseline (or typical) state of the animal; and, in response to the set of biometric data captured during the first time period deviating from the nominal set of biometric data (e.g., by greater than a threshold deviation, falling outside of the nominal range), automatically trigger the subdermal short-range wireless transmitter 114 to broadcast the set of biometric data captured during the first time period.

In particular, in this example, the biometric sensor 112 is configured to: capture a first set of data at a first time during a first time window in a first time period; capture a second set of data at a second time during a second time window in the first time period; and aggregate the first set of data and the second set of data into the set of biometric data following completion of the first time period. In particular, in this implementation, the subdermal sensor unit 110 includes a controller 116 configured to: access the set of biometric data from the biometric sensor; calculate a biometric state of the animal based on the series set of data; access a nominal state of the animal; detect a deviation between the biometric state of the animal and the nominal state of the animal; and, in response to the deviation exceeding a threshold deviation, transmit the set of biometric data and a unique identifier associated with the subdermal sensor unit 110 to the tag wireless communication module 122 via the subdermal short-range wireless transmitter 114.

Additionally or alternatively, the controller 116 of the subdermal sensor unit 110 can: inspect the set of biometric data captured by the biometric sensor 112 during the first time period; and, in response to detecting a first biometric marker (e.g., heart rate spike, blood oxygen level falling below a threshold blood oxygen level) in the set of biometric data, automatically trigger the subdermal short-range wireless transmitter 114 to broadcast the set of biometric data captured during the first time period.

Additionally or alternatively, the controller 116 of the subdermal sensor unit 110 can: during a first time period including a sampling time period defined by the sampling schedule, trigger the biometric sensor 112 to capture a first set of biometric data from under skin of the animal; access an initial set of biometric data captured during an initial time period preceding the first time period and transmitted to the superficial tag 120; and, in response to the set of biometric data captured during the first time period deviating from the initial set of biometric data (e.g., by greater than a threshold deviation, falling outside of the initial range), automatically trigger the subdermal short-range wireless transmitter 114 to broadcast the set of biometric data captured during the first time period.

In one variation, the superficial tag 120 includes a controller 126 configured to: access a sampling schedule defining sampling time windows and/or sampling time periods for the subdermal sensor unit 110 to capture biometric data; in response to detection of a first time period including a sampling time period defined by the sampling schedule, trigger a first signal to the subdermal sensor unit 110 to prompt the biometric sensor 112 to capture a set of biometric data from under skin of the animal. In particular, in this variation, the controller 126 of the superficial tag 120 can: access a sampling schedule defining sampling time windows and/or sampling time periods for the subdermal sensor unit 110 to capture biometric data; in response to detection of a first time period including a sampling time period defined by the sampling schedule, trigger a first signal to the subdermal sensor unit 110 to prompt the biometric sensor 112 to capture a set of biometric data from under skin of the animal; access a nominal set of biometric data representing a baseline (or typical) state of the animal; receive the set of biometric data from a subdermal short-range wireless transmitter 114 of the subdermal sensor unit 110; and, in response to the set of biometric data captured during the first time period deviating from the nominal set of biometric data (e.g., by greater than a threshold deviation, falling outside of the nominal range), automatically trigger the tag wireless communication module 122 to broadcast the set of biometric data captured during the first time period (e.g., to a remote access point).

Additionally or alternatively, in this variation, the superficial tag 120 can include: a battery 125; an inductive charging cell 128 configured to transmit power from the battery 125 to the inductive charging coil 118 of the subdermal sensor unit 110; and a controller 126. In particular, the controller 126 of the superficial tag 120 is configured to: access a sampling schedule; and trigger the inductive charging cell 128 to transmit power from the battery 125 to the inductive charging coil 118 of the subdermal sensor unit 110 to activate the subdermal sensor unit 110, during a sampling period according to the sampling schedule. Additionally, in the foregoing example, the subdermal sensor unit 110 is configured to: activate upon receiving power from the battery 125 via the inductive charging coil 118; capture the set of biometric data, via the biometric sensor, upon activation; and transmit the set of biometric data to the superficial tag 120 during the sampling period.

Accordingly, in response to detecting a sampling time period (e.g., according to a sampling schedule, according to a timer within the superficial tag controller 126), the inductive charging cell 128 of the superficial tag 120 can supply power to the inductive charging coil 118 of the subdermal sensor unit 110 to thereby selectively activate the subdermal sensor unit 110 for data collection during sampling periods.

In one variation, the controller 116 of the subdermal sensor unit 110 can define a timer configured to control capture of biometric data by the subdermal sensor unit 110. For example, the controller 116 can: define a first time period (e.g., one hour); define a set of time windows (e.g., ten minute increments) within the first time period; trigger sampling of a first set of data during a first time window in the set of time windows; trigger sampling of a second set of data during a second time window in the set of time windows; compile the first set of data and the second set of data into a set of biometric data for the first time period; and, in response to completion of the first time period, broadcast the set of biometric data.

6.3 Data Communications

Generally, the subdermal short-range wireless transmitter 114 can: transmit data to a tag wireless communication module 122 via a short-form communication protocol; and the tag wireless communication module 122 can transmit data to a remote access point via a longer-form communication protocol.

In particular, the subdermal short-range wireless transmitter 114 can transmit data to a tag wireless communication module 122 via a short-form communication protocol according to a data transmission schedule (i.e., without initiation of data transmission by an interrogation signal), and the tag wireless communication module 122 can transmit data to a remote access point via a longer-form communication protocol according to a data transmission schedule (i.e., without initiation of data transmission by an interrogation signal).

For example, the superficial tag 120 can be configured to: receive the set of biometric values, the set of temperature values, and a unique identifier from the subdermal sensor unit 110 via the tag wireless communication module 122; and transmit the set of biometric values, the set of temperature values, and the unique identifier to the access point.

Additionally or alternatively, the superficial tag 120 can include: an ambient sensor 124 configured to collect a set of ambient data from an environment external the animal during the sampling period; and a geospatial location sensor 135 configured to collect a geospatial location of the animal during the sampling period. In this example, the superficial tag 120 is configured to: receive the set of biometric values, the set of temperature values, and a unique identifier from the subdermal sensor unit 110 via the tag wireless communication module 122; pair the set of biometric values and the set of temperature values with the set of ambient data and the geospatial location based on the sampling period; and transmit the set of biometric values, the set of temperature values, the set of ambient data, the geospatial location of the animal, and a unique identifier to the access point.

In one variation, the biometric sensor 112 of the subdermal sensor unit 110 is configured to capture a set of biometric data from under skin of the animal (e.g., unregulated by a sampling schedule, constant biometric data capture). In this variation, the subdermal sensor unit 110 can include a controller 116 configured to: access a data transmissions schedule defining time intervals (e.g., time windows, time periods) for transmission (e.g., offloading) of data from the subdermal short-range wireless transmitter 114 to the tag wireless communication module 122 of the superficial tag 120; and, in response to detecting a current time intersecting a first time interval defined by the data transmissions schedule, transmit a set of biometric data captured by the biometric sensor.

Additionally or alternatively, in response to the set of biometric data captured during a first time period approximating a nominal set of biometric data, the controller 116 of the subdermal sensor unit 110 can trigger the subdermal short-range wireless transmitter 114 to broadcast an acknowledgement. In this example, the superficial tag 120 can: intercept the acknowledgement broadcast by the subdermal short-range wireless transmitter 114 of the subdermal sensor unit 110; and interpret the acknowledgement as a current state of the animal approximating a baseline state of the animal and withholding additional transmission of data to the access point and/or withholding broadcasting a data sampling request to the subdermal sensor unit 110.

In one implementation, the controller 126 of the superficial tag 120 can: access a data transmission schedule; and trigger (e.g., offload) transmission of data captured by the subdermal sensor unit 110 (and/or the superficial tag 120) to a remote access point according to the data transmission schedule.

For example, the controller 126 of the superficial tag 120 can: read a first set of biometric data, broadcast by the subdermal sensor unit 110, at a first time; access a data transmission schedule; in response to the data transmission schedule excluding the first time, withhold transmission of the first set of biometric data to a remote access point; and at a second time, indicated by the data transmission schedule, trigger transmission of the first set of biometric data to a remote access point.

Additionally or alternatively, the controller 126 of the superficial tag 120 can: read a first set of biometric data, broadcast by the subdermal sensor unit 110, at a first time; detect a first deviation in the first set of biometric data from a nominal set of biometric data representing baseline values of biometrics for the animal; access a data transmission schedule; in response to the data transmission schedule excluding the first time, withhold transmission of the first set of biometric data to a remote access point; and at a second time, indicated by the data transmission schedule, trigger transmission of the first set of biometric data to a remote access point.

Additionally or alternatively, the controller 126 of the superficial tag 120 can: read a first set of biometric data, broadcast by the subdermal sensor unit 110, at a first time; access a data transmission schedule; in response to the data transmission schedule excluding the first time, withhold transmission of the first set of biometric data to a remote access point; and, at a second time indicated by the data transmission schedule, trigger transmission of an acknowledgement to a remote access point in response to absence of detection of a first deviation in the first set of biometric data from a nominal set of biometric data representing baseline values of biometrics for the animal.

Additionally or alternatively, the controller 126 can: calculate a set of metric values (e.g., heart rate, breathing rate, dissolved oxygen level) for the set of biometric data; access a range for each metric represented by the set of metric values; and broadcast the set of biometric data in response to a first metric in the set of metrics excluded from a first range associated with the first metric.

In another variation, the superficial tag 120 includes a controller 126 configured to trigger a battery 125 in the superficial tag 120 to couple an inductive charging cell 128 of the superficial tag 120. In particular, when the controller 126 triggers the battery 125 in the superficial tag 120 to couple the inductive charging cell 128 of the superficial tag 120, the inductive charging cell 128 can transmit voltage to an inductive charging coil 118 in the subdermal sensor unit 110 proximal the superficial tag 120. Additionally, once the subdermal sensor unit 110 activates in response to receiving power via the inductive charging coil 118, the subdermal sensor unit 110 can automatically initiate data sampling at the biometric sensor.

Additionally or alternatively, in this variation, the subdermal sensor unit 110 can: exclude a battery 125 and/or power storage cell; and activate (only) when the superficial tag 120 provides power (e.g., charge) to the inductive charging coil 118 of the subdermal sensor unit 110. In this variation, the superficial tag 120 can: intercept data (e.g., a stream of data) broadcast by the subdermal sensor unit 110 during data sampling; identify a data volume broadcast by the subdermal sensor unit 110 during data sampling approximating a threshold data volume; and, in response to the data volume broadcast by the subdermal sensor unit 110 exceeding the threshold data volume, cease voltage transmission from the inductive charging cell 128 to the inductive charging coil 118 to thereby cease data sampling by the subdermal sensor unit 110 by deactivating the subdermal sensor unit 110.

In one variation, the subdermal sensor unit 110 can: access a charging state of an internal battery 125 located within a housing of the subdermal sensor unit 110; and broadcast a request for power via the subdermal short-range wireless transmitter 114. In this variation, the superficial tag 120 can: intercept the request for power; and couple the battery 125 to the inductive charging cell 128 to transmit charge to the inductive charging coil 118 in the subdermal sensor unit 110 to recharge the internal battery 125 of the subdermal sensor unit 110.

Additionally or alternatively, the subdermal sensor unit 110 can broadcast a set of data packets including biometric data, a unique identifier, and a battery 125 charge state.

The superficial tag 120 can: intercept the set of data packets; read the battery 125 charge state of the subdermal sensor unit 110; and, in response to the battery 125 charge state of the subdermal sensor unit 110 falling below a threshold battery 125 charge state, couple the battery 125 to the inductive charging cell 128 to transmit charge to the inductive charging coil 118 in the subdermal sensor unit 110 to recharge the internal battery 125 of the subdermal sensor unit 110.

6.4 Data Manipulation: Calculations

Generally, the subdermal sensor unit 110 and the superficial tag 120 can coordinate to calculate metrics for the animal based on biometric data captured by the subdermal sensor unit 110 and ambient data captured by the superficial tag 120. In particular, the subdermal sensor unit 110 and the superficial tag 120 can coordinate to: capture a set of biometric data from under skin of the animal via a biometric sensor 112 arranged within the subdermal sensor unit 110; calculate a set of metric values (e.g., heart rate, breathing rate, pulse oxidation, heart function, internal temperature); normalize these metric values according to ambient data (e.g., location, external temperature, topography); and transmit these metric values to an access point for access by a remote computer system.

In one implementation, the subdermal sensor unit 110 can: calculate a set of metric values based on the set of biometric data captured by the biometric sensor 112 during a sampling period; and broadcast the set of metric values via the subdermal short-range wireless transmitter 114.

In particular, in this implementation, following conclusion of the first time window and based on the set of biometric data, the subdermal sensor unit 110 can calculate: a first heart rate of the animal; a first breathing rate of the animal; and a first dissolved oxygen level of the animal. In particular, the subdermal sensor unit 110 can include a controller 116 configured to: detect a first frequency of light absorption changes during a sampling period; calculate the first heart rate of the animal proportional to the first frequency of light absorption changes; calculate the first breathing rate of the animal proportional to the first frequency of light absorption changes; detect a first blood color—representing oxygenation of blood cells proximal the optical sensor of the subdermal sensor unit 110—within the set of biometric data; and calculate a first dissolved oxygen level of the animal based on the first blood color. In this implementation, the subdermal sensor unit 110 can: generate a set of data packets including the set of metric values; and broadcast the set of data packets. In particular, the subdermal sensor unit 110 can generate the set of data packets including: the first heart rate of the animal; the first breathing rate of the animal; and the first dissolved oxygen level of the animal.

In another implementation, the superficial tag 120 can: receive a set of biometric data from the subdermal short-range wireless transmitter 114 of the subdermal sensor unit 110; calculate a set of metric values based on the set of biometric data; and transmit the set of metric values to a remote access point. In one example, the subdermal sensor unit 110 can include: a temperature sensor configured to read an internal temperature of the animal during a sampling period; and an optical biometric sensor 112 configured to collect a set of optical data from the ear of the animal during a sampling period. In this example, the subdermal short-range wireless transmitter 114 can: transmit the internal temperature, the set of optical data, and a unique identifier associated with the subdermal sensor unit 110 to the tag wireless communication module 122 following conclusion of the sampling period. Additionally, in this example, the superficial tag 120 includes a controller 126 configured to: calculate a heart rate of the animal during the sampling period based on the set of optical data; calculate a breathing rate of the animal during the sampling period based on the set of optical data; and calculate a dissolved oxygen level value for the animal during the sampling period based on the set of optical data. In this example, the tag wireless communication module 122 can: transmit the heart rate of the animal, the breathing rate of the animal, the dissolved oxygen level value, the internal temperature, and the unique identifier associated with the subdermal sensor unit 110 to the access point.

Additionally or alternatively, the superficial tag 120 can (e.g., at a tag controller); access a set of external data captured by an external sensor (e.g., an accelerometer) arranged within the superficial tag 120; extract a set of features from the set of external data; derive a set of animal behaviors (e.g., eating time, rumination time, walking time) based on the set of features extracted from the set of external data. In this variation, the superficial tag 120 can derive the set of animal behaviors based on position data extracted from the set of external data. The superficial tag 120 can then transmit the set of animal behaviors to the access point as described herein.

In particular, the superficial tag 120 can execute Blocks of the method S100 to, based on the set of biometric data, calculate: a first heart rate of the animal; a first breathing rate of the animal; and a first dissolved oxygen level of the animal. In particular, the superficial tag 120 can, based on the set of biometric data captured by an optical sensor: detect a first frequency of light absorption changes during a sampling period; calculate the first heart rate of the animal proportional to the first frequency of light absorption changes; calculate the first breathing rate of the animal proportional to the first frequency of light absorption changes; detect a first blood color—representing oxygenation of blood cells proximal the optical sensor of the subdermal sensor unit 110—within the set of biometric data; and calculate a first dissolved oxygen level of the animal based on the first blood color.

Additionally or alternatively, in this implementation, the superficial tag 120 can: access a nominal heart rate range for the animal; and transmit the set of data packets to the access point at the second power level, greater than the first power level, via the long-range wireless communication protocol in response to the nominal heart rate range excluding the first heart rate.

Accordingly, in the foregoing implementations, the subdermal sensor unit 110 and the superficial tag 120 can coordinate to calculate biometric values for the animal based on biometric data captured by the biometric sensor 112 within the subdermal sensor unit 110.

7. Data Offloading and Presentation

Generally, the tag wireless communication module 122 can transmit data (e.g., captured by the subdermal sensor unit 110, captured by the superficial tag 120) to a remote access point proximal (e.g., within two miles) the superficial tag 120 at a second power level via a longer-range wireless communication protocol. In particular, the system can include an operator portal 140: accessible via a computing device (e.g., a mobile device); and configured to access a corpus of sets of biometric data, associated with the unique identifier; and configured to render timeseries of average internal body temperature, heart rate, heart rate variability, breathing rate, and average dissolved blood oxygen of the animal based on the corpus of sets of biometric data.

Additionally, a remote computer system, in communication with the superficial tag 120 and/or the access point and configured to receive data sampled from an animal (or a herd of animals), can calculate metrics based on these data and present the data to a user. In particular, the remote computer system can, for a first animal in a herd of animals: compile a corpus of biometric data captured over a corpus of time periods; generate a timeseries visualization of the corpus of biometric data according to the corpus of time periods; and render the timeseries visualization in a user portal.

In one implementation, a remote computer system can: access the set of biometric values, the set of temperature values, and a unique identifier via the access point; access a series of biometric values and a series of temperature values associated with the unique identifier and associated with a series of time windows preceding the sampling period; and populate a timeseries data table with the series of biometric values, the series of temperature values, the set of biometric values, and the set of temperature values according to the series of time windows and the sampling period.

Additionally or alternatively, the remote computer system can: access the set of biometric values, the set of temperature values, the set of ambient data, the geospatial location of the animal, and the unique identifier via the access point; access a series of biometric values and a series of temperature values associated with the unique identifier and associated with a series of time windows preceding the sampling period; and populate a timeseries data table with the series of biometric values, the series of temperature values, the set of biometric values, the set of temperature values according to the series of time windows and the sampling period.

For example, the remote computer system can: access a first heart rate of the animal, a first breathing rate of the animal, and a first dissolved oxygen level of the animal; access a series of heart rate values, a series of breathing rate values, and a series of dissolved oxygen level values associated with the unique identifier and associated with a series of time windows preceding the sampling period; and populate a timeseries data table with the first heart rate of the animal, the first breathing rate of the animal, the first dissolved oxygen level of the animal, the series of heart rate values, the series of breathing rate values, and the series of dissolved oxygen level values according to the series of time windows and the sampling period.

In particular, in this example, the remote computer system can execute Blocks of the method S100 to: access a set of data packets via the access point; based on the set of biometric data extracted from the set of data packets, calculate a first heart rate of the animal, a first breathing rate of the animal, and a first dissolved oxygen level value of the animal; access a series of heart rates, a series of breathing rates, a series of dissolved oxygen level values, and a series of temperature values associated with a series of time windows preceding the first time window and associated with the unique identifier; populate a timeseries data table with the series of heart rates, the series of breathing rates, the series of dissolved oxygen level values, and the series of temperature values according to the series of time windows; and populate the timeseries data table with the first heart rate of the animal, the first breathing rate of the animal, the first dissolved oxygen level value of the animal, and the internal temperature of the animal according to the first time window.

In one implementation, the remote computer system can annotate the timeseries data table and/or visualization with the set of animal behaviors (e.g., a position and/or action of the animal) based on the set of accelerometer data collected at the superficial tag 120.

Accordingly, after transmission of the data to an access point via the tag wireless communication module 122, a remote computer system can: access these data captured by subdermal sensor units 110 deployed in a herd of animals; generate visualizations representing these data; and present these visualizations to an operator.

8. Variation: Spring-Loaded Superficial Tag

In one variation, the superficial tag 120 can include a spring element 132 configured to bias the superficial tag 120 toward the ear of the animal. In particular, the tag housing 121 can include: a first spring element 132 arranged within a proximal side of the tag housing 121; and a second spring element 132 arranged within a distal side of the tag housing 121. The first spring element 132 and the second spring element 132 can coordinate to: bias the superficial tag 120 toward an ear of the animal such that the superficial tag 120 remains in contact with the ear of the animal.

In particular, the first spring element 132 and the second spring element 132 can cooperate to bias the superficial tag 120 against the ear of the animal in order to maintain proximity of the subdermal sensor unit and the superficial tag, thereby maintaining wireless connectivity between the subdermal short-range wireless transmitter 114 and the tag wireless communication module 122, such as within a transmission range of the subdermal short-range wireless transmitter 114 according to the short-range wireless communication protocol. In particular, the spring element 132 can be configured to: be sealed in the tag housing 121; and exert a first force on the ear of the animal to retain a position of the superficial tag 120 on the ear of the animal proximal the subdermal sensor unit 110.

For example, the spring element 132 can exert a first force against a surface of the ear, thereby biasing the tag toward the subdermal sensor unit 110 injected into the ear of the animal. Accordingly, the spring element 132 can maintain contact between the superficial tag and the skin of the ear of the animal, thereby flattening the ear against the superficial tag, supporting the elongate subdermal sensor unit under the skin of the ear, minimizing a distance between the subdermal sensor unit (e.g., the wireless transmitter of the subdermal sensor unit) and the superficial tag (e.g., the wireless receiver of the superficial tag), and preserving wireless connectively between the subdermal short-range wireless transmitter 114 and the superficial wireless communication module 114 over time.

Therefore, by maintaining proximity between the superficial tag 120 and the subdermal sensor unit 110, the spring element 132 can (passively) maintain connectivity between the subdermal short-range wireless transmitter 114 and the tag wireless communication module 122 to thereby reduce power required by the subdermal sensor unit 110 to transmit data to the superficial tag 120 according to the short-range wireless communication protocol.

9. Variation: Virtual Fencing

In one variation, the subdermal sensor unit 110 and the superficial tag 120 can coordinate to: identify a geospatial location of the animal; and, in response to a geospatial boundary excluding the geospatial location of the animal, trigger feedback (e.g., auditory, haptic) into the ear of the animal to direct the animal within the geospatial boundary, such as to "herd" the animal to a particular location.

9.1 Virtual Fencing: Electrode Feedback

In one example, the superficial tag 120 can: include a set of capacitive coupling elements (e.g., electrode, parallel plate capacitors, interdigitated electrode array); detect a first geospatial location of the animal at a first time; access a geospatial boundary for the animal; and, in response to the geospatial boundary excluding the first geospatial location, trigger capacitive feedback on the ear of the animal via the set of capacitive coupling elements.

9.2 Virtual Fencing: Haptic Feedback

In another variation, the superficial tag 120 can: include a haptic feedback module 134 and a geospatial location sensor 135; detect a first geospatial location of the animal based on the geospatial location sensor 135; access a geospatial boundary (e.g., virtual corral) for the animal; and, in response to the geospatial boundary excluding the first geospatial location, trigger haptic feedback via the haptic feedback module 134. In particular, in this variation, the superficial tag 120 can include: a haptic feedback module 134; a geospatial location sensor 135; and a controller 126. The controller 126 of the superficial tag 120 can be configured to: read geospatial locations of the animal from the geospatial location sensor 135; access a geospatial boundary representing bounds of geospatial locations for the animal; in response to detecting a first geospatial location of the animal, from the geospatial location sensor 135, excluded from the geospatial boundary at a first time, trigger the haptic feedback module 134 to output haptic feedback into the ear of the animal; and, in response to detecting a second geospatial location of the animal, from the geospatial location sensor 135, included in the geospatial boundary at a second time following the first time, cease haptic feedback into the ear of the animal via the haptic feedback module 134.

9.3 Virtual Fencing: Audio Feedback

In another variation, the superficial tag 120 can: include an audio feedback module 134; detect a first geospatial location of the animal based on the geospatial location sensor 135; access a geospatial boundary (e.g., virtual corral) for the animal; and, in response to the geospatial boundary excluding the first geospatial location, trigger auditory feedback via the audio feedback module 134. In particular, in this variation, the superficial tag 120 can include: an audio module; a geospatial location sensor 135; and a controller 126. The controller 126 of the superficial tag 120 can be configured to: read geospatial locations of the animal from the geospatial location sensor 135; access a geospatial boundary representing (acceptable) bounds of geospatial locations for the animal; in response to detecting a first geospatial location of the animal, from the geospatial location sensor 135, excluded from the geospatial boundary, trigger the audio module to output audio feedback into the ear of the animal; and, in response to detecting a second geospatial location of the animal, from the geospatial location sensor 135, included in the geospatial boundary at a second time following the first time, cease audio feedback into the ear of the animal via the audio module. In one variation, the controller 126 can trigger the audio module to output audio feedback into the ear of the animal to direct the animal toward the geospatial boundary.

9.4 Virtual Fencing: Thresholds

In the foregoing variations, the superficial tag 120 can access the geospatial boundary defined by a user and/or defined by a wireless communication distance threshold defined by the tag wireless communication module 122 of the superficial tag 120.

For example, a remote computer system in communication with a set of superficial tags 120 (e.g., via an access point) can: access a geospatial location of the access point configured to receive data transmissions from superficial tags 120 installed on animals; access a range of data transmission associated with the longer-range wireless communication protocol; calculate a maximum radius of data transmission from superficial tags 120 to the access point according to the range of data transmission associated with the longer-range wireless communication protocol; and define the herd boundary based on the maximum radius of data transmission concentric with the access point and representing reliable communication distance between the access point and superficial tags 120.

Additionally or alternatively, the superficial tag 120 can access the geospatial boundary defined by a user. In particular, the remote computer system can: receive a geospatial boundary representing allowable roaming bounds for a set of animals via a user portal.

In the foregoing variations, the superficial tag 120 can, after triggering feedback (e.g., electric, haptic, audio): monitor (or track) a geospatial location of the animal during a sampling period; in response to detecting a pathway traversed by the animal deviating further from the geospatial boundary, increase an intensity of feedback; in response to detecting the pathway traversed by the animal approaching the geospatial boundary, decrease an intensity of feedback; and, in response to detecting a second geospatial location of the animal included within the geospatial boundary, cease feedback.

In particular, the subdermal sensor unit 110 and the superficial tag 120 can execute Blocks of the method S100 to: at a first time, access a first geospatial location of the animal; access a geospatial boundary representing bounds of geospatial locations for the animal; in response to the geospatial boundary excluding the first geospatial location of the animal, trigger a haptic feedback module 134 to output haptic feedback into an ear of the animal; at a second time following the first time, access a second geospatial location of the animal; in response to the geospatial boundary including the second geospatial location of the animal, cease haptic feedback into the ear of the animal via the haptic feedback module 134.

Accordingly, the superficial tag 120 and the remote computer system can coordinate to maintain geospatial locations of a set (or herd) of animals within a particular geospatial boundary defined by a user and/or a threshold communication distance between tag wireless communication modules 122 within superficial tags 120 deployed on the set of animals to thereby maintain wireless communication between these superficial tags 120 and the remote access point.

The systems and methods described herein can be embodied and/or implemented at least in part as a machine configured to receive a computer-readable medium storing computer-readable instructions. The instructions can be executed by computer-executable components integrated with the application, applet, host, server, network, website, communication service, communication interface, hardware/firmware/software elements of a user computer or mobile device, wristband, smartphone, or any suitable combination thereof. Other systems and methods of the embodiment can be embodied and/or implemented at least in part as a machine configured to receive a computer-readable medium storing computer-readable instructions. The instructions can be executed by computer-executable components integrated by computer-executable components integrated with apparatuses and networks of the type described above. The computer-readable medium can be stored on any suitable computer readable media such as RAMs, ROMs, flash memory, EEPROMs, optical devices (CD or DVD), hard drives, floppy drives, or any suitable device. The computer-executable component can be a processor, but any suitable dedicated hardware device can (alternatively or additionally) execute the instructions.

As a person skilled in the art will recognize from the previous detailed description and from the figures and claims, modifications and changes can be made to the embodiments of the invention without departing from the scope of this invention as defined in the following claims.

We claim:

1. A system comprising:
a subdermal sensor unit:
injectable under skin of an ear of an animal; and
comprising:
a subdermal housing;
a set of biometric sensors sealed in the subdermal housing; and
a wireless charging coil:
sealed in the subdermal housing; and
configured to:
receive energy from a wireless charging cell of a superficial tag installed proximal the subdermal sensor unit; and
stream a set of biometric data, captured by the set of biometric sensors, via a short-range wireless communication protocol responsive to receiving power from the wireless charging cell;
a local energy store configured to store energy received from the wireless charging cell, via a magnetic field, during a first time period; and
a local memory unit configured to store biometric sensor data captured by the set of biometric sensors during a second time period succeeding the first time period; and
wherein the wireless charging coil is configured to transmit the set of biometric data, stored in the local memory unit, to the superficial tag via load modulation of the magnetic field during a third time period succeeding the second time period; and
the superficial tag comprising:
a tag housing;
the wireless charging cell:
located within the housing; and
configured to:
transmit energy to the subdermal sensor unit by inducing the magnetic field between the wireless charging cell and the wireless charging coil; and
receive the set of biometric data transmitted by the wireless charging coil in the subdermal sensor unit; and
a tag wireless communication module:
located within the housing; and
configured to transmit the set of biometric data to an access point via a longer-range wireless communication protocol.

2. The system of claim 1, wherein the subdermal sensor unit is configured to:
store a sampling schedule in the local memory unit;
based on the sampling schedule:
transition from an inactive state to an active state during a first sampling interval within the second time period;
capture a first set of biometric data during the first sampling interval;
store the first set of biometric data in the local memory unit;
return to the inactive state following the first sampling interval;
transition from the inactive state to the active state during a second sampling interval within the second time period;
capture a second set of biometric data during the second sampling interval;
store the second set of biometric data in the local memory unit; and
return to the inactive state following the second sampling interval; and
responsive to receiving energy from the inductive charging cell of the superficial tag, transmit the first set of biometric data and the second set of biometric data from the local memory unit to the superficial tag.

3. A system comprising:
a subdermal sensor unit:
injectable under skin of an ear of an animal; and
comprising:
a subdermal housing;
a set of biometric sensors:
sealed in subdermal housing; and
comprising:
a temperature sensor configured to sense internal body temperatures of the animal; and
an optical biometric sensor configured to sense dissolved blood oxygen levels of the animal; and
a subdermal short-range wireless transmitter:
sealed in the subdermal housing; and
configured to stream a set of biometric data, representing internal body temperatures and dissolved blood oxygen levels of the animal during a sampling period and captured by the set of biometric sensors, and a unique identifier associated with the subdermal sensor unit at a first power level via a short-range wireless communication protocol during the sampling period;

a superficial tag comprising:
a tag housing;
a controller configured to:
calculate an average internal body temperature during the sampling period based on the set internal body temperatures; and
calculate a heart rate, a heart rate variability, a breathing rate, and an average dissolved blood oxygen rate of the animal during the sampling period based on the set of optical data;
a tag wireless communication module:
sealed within the tag housing;
configured to receive the set of biometric data broadcast by the subdermal short-range wireless transmitter in the subdermal sensor unit; and
configured to transmit the unique identifier and the average internal body temperature, the heart rate, the heart rate variability, the breathing rate, and the average dissolved blood oxygen rate of the animal during the sampling period to an access point at a second power level, greater than the first power level, via a longer-range wireless communication protocol; and
a set of barbs configured to pass through the ear of the animal to:
retain the tag housing to the ear of the animal; and
locate the tag wireless communication module over the subdermal short-range wireless transmitter of the subdermal sensor unit to maintain wireless connectivity between the subdermal short-range wireless transmitter and the tag wireless communication module; and
an operator portal:
accessible via a computing device; and
configured to:
access a corpus of sets of biometric data, associated with the unique identifier; and
render timeseries of average internal body temperature, heart rate, heart rate variability, breathing rate, and average dissolved blood oxygen of the animal based on the corpus of sets of biometric data.

4. A system comprising:
a subdermal sensor unit:
injectable under skin of an ear of an animal; and
comprising:
a subdermal housing;
a set of biometric sensors sealed in subdermal housing; and
a subdermal short-range wireless transmitter:
sealed in the subdermal housing; and
configured to broadcast a set of biometric data, captured by the set of biometric sensors, at a first power level via a short-range wireless communication protocol; and
a local memory store module; and
an inductive charging coil configured to receive energy from a battery in the superficial tag via an inductive charging cell;
a superficial tag comprising:
a tag housing;
a tag wireless communication module:
sealed within the tag housing;
configured to receive the set of biometric data broadcast by the subdermal short-range wireless transmitter in the subdermal sensor unit; and
configured to transmit the set of biometric data to an access point at a second power level, greater than the first power level, via a longer-range wireless communication protocol;
the battery;
the inductive charging cell configured to transmit energy from the battery to the inductive charging coil of the subdermal sensor unit; and
a controller configured to:
access a sampling schedule; and
trigger the inductive charging cell to transmit energy from the battery to the inductive charging coil of the subdermal sensor unit, during sampling periods defined by the sampling schedule, to activate the subdermal sensor unit; and
a set of barbs configured to pass through the ear of the animal to:
retain the tag housing to the ear of the animal; and
locate the tag wireless communication module over the subdermal short-range wireless transmitter of the subdermal sensor unit to maintain wireless connectivity between the subdermal short-range wireless transmitter and the tag wireless communication module; and
wherein the subdermal sensor unit is configured to:
receive energy via the inductive charging cell of the superficial tag during a first sampling period;
via the set of biometric sensors, capture a first set of biometric data during the first sampling period;
store the first set of biometric data in the local memory store during the first sampling period;
receive energy via the inductive charging cell of the superficial tag during a second sampling period;
via the set of biometric sensors, capture a second set of biometric data during the second sampling period;
store the second set of biometric data in the local memory store during the second sampling period; and
broadcast the first set of biometric data and a unique identifier associated with the subdermal sensor unit to the tag wireless communication module during the second sampling period.

5. A system comprising:
a subdermal sensor unit:
injectable under skin of an ear of an animal; and
comprising:
a subdermal housing;
a set of biometric sensors sealed in subdermal housing; and
a subdermal short-range wireless transmitter:
sealed in the subdermal housing; and
configured to broadcast a set of biometric data, captured by the set of biometric sensors, at a first power level via a short-range wireless communication protocol; and
a superficial tag comprising:
a flexible printed circuit board configured to elastically conform to the ear of the animal;
a tag housing encasing the flexible printed circuit board;
a tag wireless communication module:
sealed within the tag housing and arranged on the flexible printed circuit board;
configured to receive the set of biometric data broadcast by the subdermal short-range wireless transmitter in the subdermal sensor unit; and configured to transmit the set of biometric data to an access point at a second power level, greater than the first power level, via a longer-range wireless communication protocol;

a spring element:

interposed between the tag housing and the flexible printed circuit board; and configured to bias the flexible printed circuit board against the ear of the animal to maintain proximity of the wireless communication module in the superficial tag to the subdermal short-range wireless transmitter in the subdermal sensor unit; and a set of barbs configured to pass through the ear of the animal to:

retain the tag housing to the ear of the animal;

locate the tag wireless communication module over the subdermal short-range wireless transmitter of the subdermal sensor unit; and cooperate with the spring element to maintain wireless connectivity between the subdermal short-range wireless transmitter and the tag wireless communication module.

6. A system comprising:

a subdermal sensor unit:

comprising:

a subdermal housing;

a set of biometric sensors sealed in subdermal housing; and a subdermal short-range wireless transmitter:

sealed in the subdermal housing; and configured to broadcast a set of biometric data, captured by the set of biometric sensors, at a first power level via a short-range wireless communication protocol; and a polymer encasing the set of biometric sensors and the subdermal short-range wireless transmitter;

defining a lozenge geometry characterized by a width less than 5/32 of an inch; and configured to inject under skin of an ear of an animal via a six-gauge hypodermic needle, the animal comprising a domesticated bovid ungulate;

a superficial tag comprising:

a tag housing;

a tag wireless communication module:

sealed within the tag housing;

configured to receive the set of biometric data broadcast by the subdermal short-range wireless transmitter in the subdermal sensor unit; and configured to transmit the set of biometric data to an access point at a second power level, greater than the first power level, via a longer-range wireless communication protocol;

a light element configured to:

illuminate in a first color responsive to absence of beacon signals received by the tag wireless communication module and emitted from the subdermal sensor unit; and illuminate in a second color responsive to detection of a beacon signal received at the tag wireless communication module and emitted from the subdermal sensor unit; and a set of barbs configured to pass through the ear of the animal to:

retain the tag housing to the ear of the animal; and locate the tag wireless communication module over the subdermal short-range wireless transmitter of the subdermal sensor unit to maintain wireless connectivity between the subdermal short-range wireless transmitter and the tag wireless communication module.

7. A system comprising:

a subdermal sensor unit:

characterized by a first length;

injectable under skin of an ear of an animal; and comprising:

a first end and a second end;

a subdermal housing;

a set of biometric sensors sealed in subdermal housing; and a subdermal short-range wireless transmitter:

sealed in the subdermal housing; and configured to broadcast a set of biometric data, captured by the set of biometric sensors, at a first power level via a short-range wireless communication protocol; and a superficial tag comprising:

a tag housing;

a tag wireless communication module:

sealed within the tag housing;

configured to receive the set of biometric data broadcast by the subdermal short-range wireless transmitter in the subdermal sensor unit; and configured to transmit the set of biometric data to an access point at a second power level, greater than the first power level, via a longer-range wireless communication protocol; and a set of barbs:

comprising:

a first barb; and a second barb laterally offset from the first barb by a first distance greater than the first length of the subdermal sensor unit configured to pass through the ear of the animal to:

retain the tag housing to the ear of the animal with the first barb, the second barb, the first end of the subdermal sensor, and the second end of the subdermal sensor aligned approximately colinearly;

interfere with axial migration of the subdermal sensor unit within the ear of the animal; and locate the tag wireless communication module over the subdermal short-range wireless transmitter of the subdermal sensor unit to maintain wireless connectivity between the subdermal short-range wireless transmitter and the tag wireless communication module.

8. A system comprising:

a subdermal sensor unit:

injectable under skin of an ear of an animal; and comprising:

a subdermal housing;

a set of biometric sensors sealed in subdermal housing, the set of biometric sensors comprising:

a temperature sensor; and an optical biometric sensor;

a controller configured to:

read a set of internal body temperatures of the animal, during a sampling period, from the temperature sensor;

read a set of optical data, representing heart rate, breathing rate, and dissolved blood oxygen of the animal during the sampling period, from the optical biometric sensor;

calculate an average internal body temperature during the sampling period based on the set internal body temperatures; and derive a heart rate, a heart rate variability, a breathing rate, and an average dissolved blood oxygen rate of the animal during the sampling period based on the set of optical data; and a subdermal short-range wireless transmitter:

sealed in the subdermal housing; and configured to broadcast a set of biometric data and a unique identifier associated with the subdermal sensor unit to the tag wireless communication module, the set of biometric data comprising the average internal body temperature, the heart rate, the heart rate variability, the breathing rate, and the average dissolved blood oxygen rate of the animal, at a first power level via a short-range wireless communication protocol; and a superficial tag comprising:

a tag housing;

an external sensor configured to capture a set of external data;

a tag wireless communication module:

sealed within the tag housing;

configured to receive the set of biometric data broadcast by the subdermal short-range wireless transmitter in the subdermal sensor unit; and configured to transmit the set of external data and the set of biometric data, associated with the unique identifier, to an access point at a second power level, greater than the first power level, via a longer-range wireless communication protocol; and a set of barbs configured to pass through the ear of the animal to:

retain the tag housing to the ear of the animal; and locate the tag wireless communication module over the subdermal short-range wireless transmitter of the subdermal sensor unit to maintain wireless connectivity between the subdermal short-range wireless transmitter and the tag wireless communication module.

9. The system of claim 8:

wherein the subdermal sensor unit further comprises an inductive charging coil;

wherein the superficial tag further comprises:

a battery;

an inductive charging cell configured to transmit energy from the battery to the inductive charging coil of the subdermal sensor unit; and a controller configured to:

access a sampling schedule; and trigger the inductive charging cell to transmit energy from the battery to the inductive charging coil of the subdermal sensor unit, during a sampling period defined by the sampling schedule, to activate the subdermal sensor unit; and wherein the subdermal sensor unit is configured to:

transition from an inactive state into an active state responsive to receiving energy from the superficial tag via the inductive charging cell;

capture the set of biometric data, via the set of biometric sensors, in the active state; and broadcast the set of biometric data, via the subdermal short-range wireless transmitter, during the sampling period.

10. The system of claim 9:

wherein the subdermal sensor unit is configured to transition from the active state into the inactive state responsive to cessation of energy transmission from the superficial tag via the inductive charging cell.

11. The system of claim 9:

wherein the subdermal short-range wireless transmitter and the inductive charging coil of the subdermal sensor unit are physically coextensive;

wherein the inductive charging cell and the tag wireless communication module of the superficial tag are physically coextensive;

wherein the inductive charging cell of the superficial tag is configured to transmit energy to the subdermal sensor unit by inducing a magnetic field between the inductive charging cell and the inductive charging coil; and wherein the inductive charging coil of the subdermal sensor unit is configured to broadcast the set of biometric data via load modulation of the magnetic field.

12. The system of claim 8:

wherein the subdermal short-range wireless transmitter of the subdermal sensor unit is configured to stream the set of biometric data, representing internal body temperatures and dissolved blood oxygen levels of the animal during a sampling period, and the unique identifier associated with the subdermal sensor unit during the sampling period;

wherein the tag wireless communication module of the superficial tag is configured to transmit the unique identifier and the average internal body temperature, the heart rate, the heart rate variability, the breathing rate, and the average dissolved blood oxygen rate of the animal during the sampling period to the access point; and further comprising an operator portal:

accessible via a computing device; and configured to:

access a corpus of sets of biometric data, associated with the unique identifier; and render timeseries of average internal body temperature, heart rate, heart rate variability, breathing rate, and average dissolved blood oxygen of the animal based on the corpus of sets of biometric data.

13. The system of claim 8:

wherein the subdermal sensor unit further comprises:

a local energy store module distinct from the subdermal short-range wireless transmitter; and a local memory store module:

distinct from the subdermal short-range wireless transmitter; and configured to store the set of biometric data comprising the average internal body temperature, the heart rate, the heart rate variability, the breathing rate, and the average dissolved blood oxygen rate of the animal; and wherein the subdermal short-range wireless transmitter is configured to:

broadcast the set of biometric data and a unique identifier associated with the subdermal sensor unit to the tag wireless communication module during a second time period following the sampling period via near-field communications.

14. The system of claim 8:
wherein the superficial tag further comprises:
a battery;
an inductive charging cell configured to transmit energy from the battery to an inductive charging coil of the subdermal sensor unit; and
a controller configured to:
access a sampling schedule; and
trigger the inductive charging cell to transmit energy from the battery to the inductive charging coil of the subdermal sensor unit, during sampling periods defined by the sampling schedule, to activate the subdermal sensor unit; and
wherein the subdermal sensor unit:
further comprises:
a local memory store module; and
the inductive charging coil configured to receive energy from the battery in the superficial tag via the inductive charging cell; and
is configured to:
receive energy via the inductive charging cell of the superficial tag during a first sampling period;
via the set of biometric sensors, capture a first set of biometric data during the first sampling period;
store the first set of biometric data in the local memory store during the first sampling period;
receive energy via the inductive charging cell of the superficial tag during a second sampling period;
via the set of biometric sensors, capture a second set of biometric data during the second sampling period;
store the second set of biometric data in the local memory store during the second sampling period; and
broadcast the first set of biometric data and a unique identifier associated with the subdermal sensor unit to the tag wireless communication module during the second sampling period.

15. The system of claim 8:
wherein the superficial tag further comprises a flexible printed circuit board configured to elastically conform to the ear of the animal;
wherein the tag wireless communication module is arranged on the flexible printed circuit board;
wherein the tag housing encases the flexible printed circuit board; and
wherein the superficial tag further comprises a spring element:
interposed between the tag housing and the flexible printed circuit board; and
configured to bias the flexible printed circuit board against the ear of the animal to:
maintain proximity of the wireless communication module in the superficial tag to the subdermal short-range wireless transmitter in the subdermal sensor unit; and
maintain wireless connectivity between the superficial tag and the subdermal sensor unit.

16. The system of claim 8:
wherein the subdermal sensor unit housing:
comprises a polymer encasing the set of biometric sensors and the subdermal short-range wireless transmitter; and
defines a lozenge geometry characterized by a width less than 5/32 of an inch; and,
wherein the subdermal sensor unit is configured to inject under the skin of the animal via a six-gauge hypodermic needle, the animal comprising a domesticated bovid ungulate; and
wherein the superficial tag further comprises a light element configured to:
illuminate in a first color responsive to absence of beacon signals received by the tag wireless communication module and emitted from the subdermal sensor unit; and
illuminate in a second color responsive to detecting detection of a beacon signal received at the tag wireless communication module and emitted from the subdermal sensor unit.

17. The system of claim 8:
wherein the superficial tag further comprises:
a haptic feedback module;
a geospatial location sensor; and
a controller configured to:
access a geospatial boundary associated with the animal;
read a first geospatial location of the animal at a first time from the geospatial location sensor;
in response to the geospatial location of the animal falling outside of the geospatial boundary, trigger the haptic feedback module to output haptic feedback;
read a second geospatial location of the animal at a second time, succeeding the first time, from the geospatial location sensor; and
in response to the second geospatial location of the animal falling within the geospatial boundary triggering the haptic feedback module to cease output of haptic feedback.

18. The system of claim 8:
wherein the subdermal sensor unit:
is characterized by a first length; and
comprising a first end and a second end; and
wherein the set of barbs:
comprises:
a first barb; and
a second barb laterally offset from the first barb by a first distance greater than the first length of the subdermal sensor unit; and
is configured to:
retain the superficial tag on the ear of the animal with the first barb, the second barb, the first end of the subdermal sensor, and the second end of the subdermal sensor aligned approximately colinearly; and
interfere with axial migration of the subdermal sensor unit within the ear of the animal.

* * * * *